US012318272B2

(12) United States Patent  
Mueller et al.

(10) Patent No.: US 12,318,272 B2  
(45) Date of Patent: Jun. 3, 2025

(54) ABSORBENT ARTICLE

(71) Applicant: Kimberly-Clark Worldwide, Inc., Neenah, WI (US)

(72) Inventors: Justin M. Mueller, Oshkosh, WI (US); Bridget Balogh, Menasha, WI (US); Marcille F. Ruman, Oshkosh, WI (US); Matthew R. Van Hout, Appleton, WI (US); Lindsay Borkovetz, Hortonville, WI (US); Jason K. Sieck, Neenah, WI (US); Jason G. Csida, Appleton, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 798 days.

(21) Appl. No.: 17/434,076

(22) PCT Filed: Feb. 28, 2019

(86) PCT No.: PCT/US2019/019983  
§ 371 (c)(1),  
(2) Date: Aug. 26, 2021

(87) PCT Pub. No.: WO2020/176098  
PCT Pub. Date: Sep. 3, 2020

(65) Prior Publication Data  
US 2022/0151840 A1 May 19, 2022

(51) Int. Cl.  
*A61F 13/496* (2006.01)  
*A61F 13/49* (2006.01)

(52) U.S. Cl.  
CPC ...... *A61F 13/496* (2013.01); *A61F 13/49017* (2013.01); *A61F 13/4902* (2013.01);  
(Continued)

(58) Field of Classification Search  
CPC .............. A61F 13/49011; A61F 13/496; A61F 13/49017; A61F 13/49019;  
(Continued)

(56) References Cited

U.S. PATENT DOCUMENTS 4,692,163 A 9/1987 Widlund et al.  
5,295,987 A 3/1994 Widlund et al.  
(Continued)

FOREIGN PATENT DOCUMENTS

WO 2004078084 A1 9/2004  
WO 2014177705 A1 11/2014

*Primary Examiner* — Guy K Townsend  
*Assistant Examiner* — Seth Han  
(74) *Attorney, Agent, or Firm* — KIMBERLY-CLARK WORLDWIDE, INC.

(57) ABSTRACT

An absorbent article has a front region, a back region, and a crotch region extending between and connecting the front region and the back region. A non-rectangular absorbent core is located in the absorbent article wherein a portion of the absorbent core is positioned in an overlapping relationship with an elastic material located in at least one of the front region or back region. The non-rectangular absorbent core has a narrowest width dimension in the transverse direction of the absorbent article which is offset from each of the transverse axis of the absorbent article and the narrowest width of the absorbent article. Longitudinally extending elastic material located in the crotch region of the absorbent article is positioned in a spaced apart relationship to the longitudinal direction side edges of the absorbent core.

20 Claims, 11 Drawing Sheets

(52) U.S. Cl.
CPC ............... *A61F 2013/49022* (2013.01); *A61F 2013/49025* (2013.01)

(58) Field of Classification Search
CPC .. A61F 2013/49036; A61F 2013/49039; A61F 2013/49041; A61F 2013/49028; A61F 2013/49025; A61F 2013/49033; A61F 13/49009; A61F 13/4902; A61F 13/49012
See application file for complete search history.

(56) References Cited

U.S. PATENT DOCUMENTS

| | | |
|---|---|---|
| 5,749,865 A | 5/1998 | Yamamoto et al. |
| 5,916,206 A | 6/1999 | Otsubo et al. |
| 6,375,646 B1 | 4/2002 | Widlund et al. |
| 6,726,669 B2 | 4/2004 | Shimada et al. |
| 6,808,582 B2 * | 10/2004 | Popp ................. A61F 13/15609 604/385.24 |
| 7,331,946 B2 | 2/2008 | Shimada et al. |
| 7,699,827 B2 | 4/2010 | Sandin et al. |
| 7,959,618 B2 | 6/2011 | Hermansson et al. |
| 8,518,010 B2 | 8/2013 | Kuwano et al. |
| 8,915,900 B2 | 12/2014 | Shimada et al. |
| 8,939,956 B2 | 1/2015 | Mukai et al. |
| 2002/0049421 A1 | 4/2002 | Hayase et al. |
| 2002/0072728 A1 | 6/2002 | Shinohara et al. |
| 2004/0225270 A1 | 11/2004 | Hermansson et al. |
| 2004/0243086 A1 | 12/2004 | VanGompel et al. |
| 2005/0080394 A1 | 4/2005 | Otsubo et al. |
| 2005/0107763 A1 | 5/2005 | Matsuda et al. |
| 2006/0025746 A1 | 2/2006 | Sasaki et al. |
| 2007/0208317 A1 | 9/2007 | Krautkramer et al. |
| 2009/0187157 A1 | 7/2009 | Hornung et al. |
| 2009/0275911 A1 | 11/2009 | Hornung et al. |
| 2010/0108554 A1* | 5/2010 | Melius ................. A61F 13/4915 604/385.28 |
| 2010/0228212 A1* | 9/2010 | Desai ................. A61F 13/49011 604/385.29 |
| 2013/0211366 A1* | 8/2013 | Gassner ............... A61F 13/5146 604/385.29 |
| 2015/0065982 A1 | 3/2015 | Hamilton et al. |
| 2015/0230996 A1 | 8/2015 | LaVon et al. |
| 2015/0272787 A1 | 10/2015 | Seitz et al. |
| 2016/0095764 A1 | 4/2016 | Seitz et al. |
| 2016/0100997 A1 | 4/2016 | Seitz et al. |
| 2017/0348158 A1* | 12/2017 | You ................... A61F 13/15804 |
| 2018/0085263 A1 | 3/2018 | Boll et al. |
| 2019/0254884 A1 | 8/2019 | Mukai et al. |

\* cited by examiner

ABSORBENT ARTICLE

BACKGROUND OF THE DISCLOSURE

Child care, feminine care, and adult hygiene-related absorbent personal care articles are often used to protect a wearer's outer garments from soiling, and to collect and retain body exudates such as menses, blood, feces, and urine. Such articles are often presented in disposable garment-like product formats (as opposed to inserts, pads, or liners) and are worn as undergarments in the place of traditional underwear. They are most commonly placed on a wearer by being pulled up about a wearer's legs towards the wearer's lower abdomen and placed adjacent a wearer's crotch region during use.

Today, many wearers of absorbent garment-like articles include adults who experience various forms of incontinence. Primary desired attributes of such garments include the garment retaining body exudate, minimal or no leakage of body exudate, close-to-body fit of the garment, and that it resembles traditional woven underwear. Consumers are interested in such attributes as there is a desire to enhance the overall personal experience of using such products while reducing incontinence-related stigma. Consumers want a garment that will meet their needs without signaling to others that they are wearing such absorbent garment-like articles. Absorbent article stigmas are aggravated by product designs which can feel bulky, may gap away from the wearer's body producing an outline that can be seen through a wearer's clothing, may be manufactured from materials that can create relatively high levels of noise during use due to the specific product construction materials, and by an overall artificial visual appearance of such products when viewed by the wearer and also by third parties.

In order to improve the fit of garment-like articles, many garment-like articles are formed by positioning an absorbent assembly between or otherwise bonded to at least one stretchable or elastomeric outer layer of the garment-like article. The stretchable or elastomeric outer layer can extend transversely and longitudinally beyond the dimensional boundaries of the absorbent assembly such as into the waist region of the garment or into areas that would contact a wearer's hips when the garment is worn. Many such garments, however, do not provide the level of comfortable discretion that is desired by consumers. Such garments generally contain large, bulky, and rectangular absorbent materials which can cause the garment to be distorted in garment fit when viewed relative to ordinary non-absorbent underwear. Such distortion is manifest as the absorbent material protruding away from the wearer's body in both the front and the back and potentially showing through tight fitting clothing during wear. Additionally, the interaction between the stretchable materials and the absorbent material can cause further protrusion of the absorbent material away from the wearer's body. Garments with active elastic materials positioned over and around the absorbent material can cause the absorbent material to bunch up and protrude away from the wearer's body while garments without active elastic materials over and around the absorbent material can fail to hold the absorbent material tight against the wearer's body also resulting in protrusion of the absorbent material away from the wearer's body. Furthermore, the size and bulk of the absorbent material can cause leg irritation to the wearer of the garment particularly in the crotch region of the garment. Many absorbent garments contain elastic materials around the leg portion of the garment which are positioned close to the absorbent material in the crotch region. Closely positioned crotch elastic materials next to the absorbent material can prevent the absorbent material from fitting close to the wearer's body and can prevent the absorbent material from moving independently from the crotch elastic materials. Such non-independence of the movement of the absorbent material can result in the absorbent material and/or crotch elastic materials rubbing against the wearer's legs during use resulting in irritation. Conversely, crotch elastic materials which are positioned too far from the absorbent material can result in the crotch region of the garment sagging away from the body of the wearer due to the weight of the absorbent material particularly after insult by body exudate. This combination of ill-fitting garment elements results in garment distortion which can lead to discomfort, irritation, and indiscretion. Such ill-fitting garments can also increase the incidence of body exudate leakage from the garment.

There is a need for an absorbent article having an improved fit about the lower torso of the wearer. There is a need for an absorbent article having targeted placement and sizing of absorbent core materials as well as of elastomeric material. Such is desirable so as to provide a more comfortable fit across different areas of a wearer's anatomy. There is a need to provide an absorbent article having an improved fit as well as the appearance of traditional woven underwear.

SUMMARY OF THE DISCLOSURE

In various embodiments, an absorbent article can have a longitudinal direction and a transverse direction; a longitudinal axis and a transverse axis; a front region comprising a first waist edge, a first longitudinal direction side edge, a second longitudinal direction side edge transversely opposed to the first longitudinal direction side edge, a front region width in the transverse direction from the first longitudinal direction side edge to the second longitudinal direction side edge; a first waist portion, a first chassis portion, a first elastic material extending continuously in the transverse direction between the first longitudinal direction side edge and the second longitudinal direction side edge in the first chassis portion; a back region comprising a second waist edge, a third longitudinal direction side edge, a fourth longitudinal direction side edge transversely opposed to the third longitudinal direction side edge, a second waist portion, a second chassis portion, a second elastic material extending continuously in the transverse direction between the third longitudinal direction side edge and the fourth longitudinal direction side edge in the second chassis portion; a first side seam formed by bonding the first longitudinal direction side edge of the front region to the third longitudinal direction side edge of the back region and a second side seam formed by bonding the second longitudinal direction side edge of the front region to the fourth longitudinal direction side edge of the back region; a crotch region located between the front region and the back region and comprising an absorbent article narrowest width in the transverse direction wherein the absorbent article narrowest width is located between the transverse axis and the first waist edge; an article length measured from the first waist edge to the second waist edge; a first article sub-length measured from the first waist edge to the absorbent article narrowest width and a second article sub-length measured from the second waist edge to the absorbent article narrowest width wherein the first article sub-length is less than the second article sub-length; an absorbent core which can have a perimeter edge comprising a first transverse direction end edge, a second transverse direction end edge opposed to the first transverse direction end edge; a first absorbent core longitudinal direction side edge, a second absorbent core longitudinal direction side edge opposed to the first longitudinal direction side edge, wherein the first longitudinal direction side edge and the second longitudinal direction side edge extend between and connect the first transverse direction end edge and the second transverse direction end edge, wherein the perimeter edge defines a non-rectangular shape of the absorbent core; an absorbent core length measured from the first transverse direction end edge to the second transverse direction end edge wherein the absorbent core length is less than 50% of the article length; a first portion of the absorbent core located in the crotch region; a second portion of the absorbent core located in a portion of at least one of the front region or the back region wherein the second portion of the absorbent core is in an overlapping configuration with at least one of a portion of the first elastic material or a portion of the second elastic material; an absorbent core narrowest width measured in the transverse direction between the first absorbent core longitudinal direction side edge and the second absorbent core longitudinal direction side edge wherein the absorbent core narrowest width is located between the absorbent article narrowest width and the transverse axis; and an absorbent core maximum width measured in the transverse direction between the first absorbent core longitudinal direction side edge and the second absorbent core longitudinal direction side edge; a first longitudinally extending elastic material located in the crotch region of the absorbent article and separated from the first longitudinal direction side edge of the absorbent core in the transverse direction at the location of each of the absorbent article narrowest width, the absorbent core narrowest width, and the transverse axis by a spatial distance of at least 1.5% of the front region width; and a second longitudinally extending elastic material location in the crotch region of the absorbent article and separated from the second longitudinal direction side edge of the absorbent core in the transverse direction at the location of each of the absorbent article narrowest width, the absorbent core narrowest width, and the transverse axis by a spatial distance of at least 1.5% of the front region width.

In various embodiments, the absorbent article narrowest width is less than 25% of the front region width.

In various embodiments, the first article sub-length is less than 45% of the article length and the second article sub-length is greater than 55% of the article length.

In various embodiments, the absorbent core narrowest width is less than 12% of the front region width. In various embodiments, the absorbent core narrowest width is less than 50% of the absorbent article narrowest width.

In various embodiments, the absorbent core maximum width is less than 25% of the front region width.

In various embodiments, the absorbent core narrowest width is less than 85% of the absorbent core maximum width. In various embodiments, the absorbent core narrowest width is offset in the longitudinal direction from the absorbent article narrowest width by a distance from 1% to 5% of the article length. In various embodiments, the absorbent core narrowest width is offset in the longitudinal direction from the transverse axis by a distance from 6% to 15% of the article length.

In various embodiments, the first longitudinally extending elastic material and the second longitudinally extending elastic material are non-linear in the longitudinal direction. In various embodiments, the first longitudinally extending elastic material and the second longitudinally extending elastic material are linear in the longitudinal direction.

In various embodiments, the first elastic material and the second elastic material is a plurality of elastomeric strands. In various embodiments, the first elastic material and the second elastic material is a polymeric film sheet.

In various embodiments, a portion of at least one of the first chassis portion or the second chassis portion has a non-uniform tension in the transverse direction. In various embodiments, a portion of at least one of the first chassis portion of the second chassis portion has a uniform tension in the transverse direction.

In various embodiments, a portion of at least one of the first chassis portion or the second chassis portion has a non-uniform tension in the longitudinal direction. In various embodiments, a portion of at least one of the first chassis portion of the second chassis portion has a uniform tension in the longitudinal direction.

In various embodiments, the back region further comprises a first leg elastic having a first tension. In various embodiments, the back region further comprises a second leg elastic having a second tension which is different from the first tension of the first leg elastic. In various embodiments, the first leg elastic has been selectively deadened.

Figure 1:
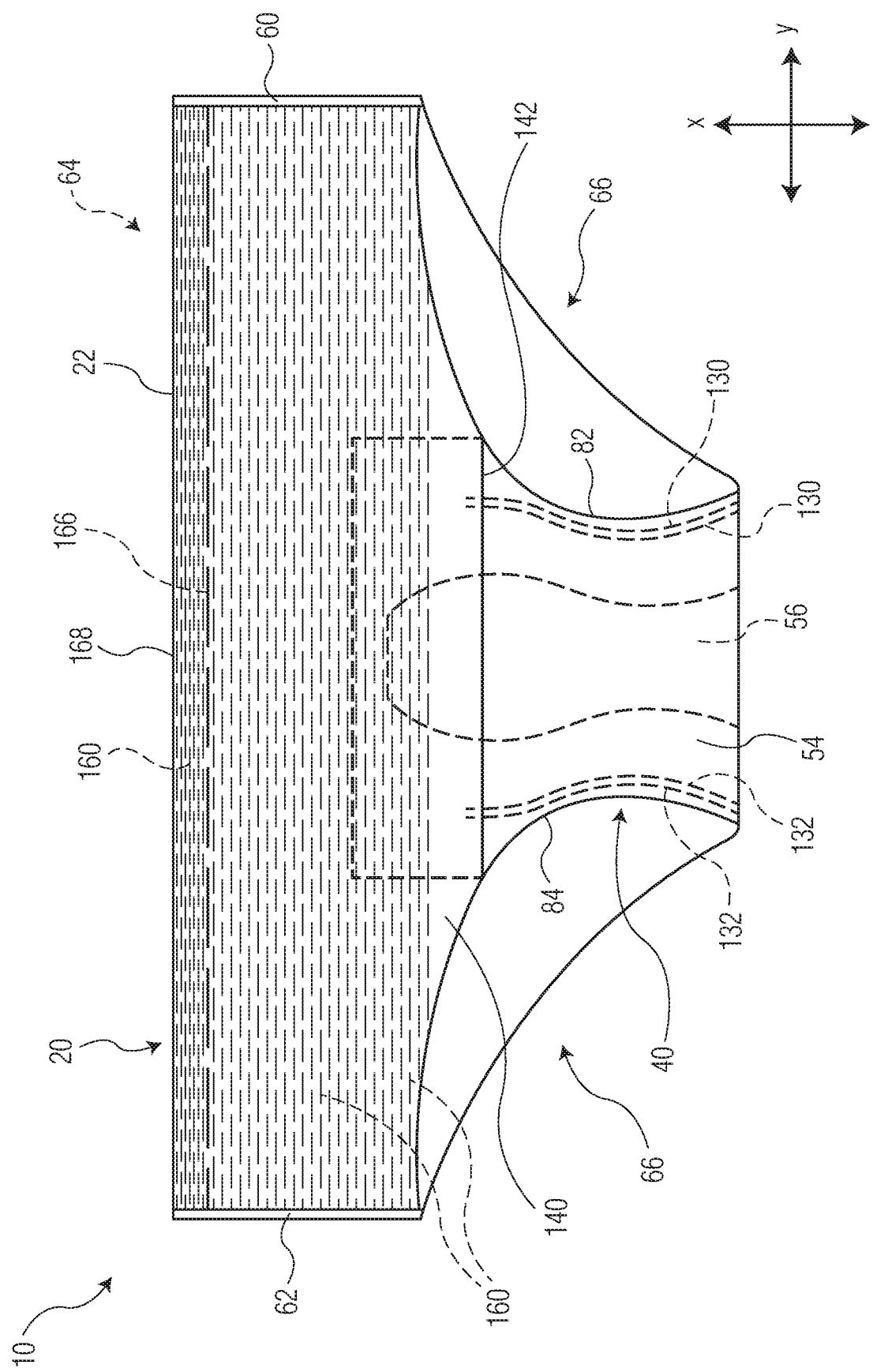
FIG. 1 is an illustration of a front view of an embodiment of an absorbent article in a pull-on, pant-like configuration.

Repeat use of reference characters in the present specification and drawings is intended to represent the same or analogous features or elements of the disclosure.

DETAILED DESCRIPTION OF THE DISLOSURE

The present disclosure is directed towards an absorbent article such as a garment-like absorbent article. The absorbent article has a front region, a back region, and a crotch region extending between and connecting the front region and the back region. A non-rectangular absorbent core is located in the absorbent article wherein a portion of the absorbent core is positioned in an overlapping relationship with an elastic material located in at least one of the front region or back region. The non-rectangular absorbent core has a narrowest width dimension in the transverse direction of the absorbent article which is offset from each of the transverse axis of the absorbent article and the narrowest width of the absorbent article. Additionally, longitudinally extending elastic material located in the crotch region of the absorbent article is positioned in a spaced apart relationship from each of the longitudinal direction side edges of the absorbent core. An absorbent article comprising such a combination of elements can provide an improved fit of the absorbent article to the body of the wearer.

As used herein, the term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, enuresis garments, menstrual pants, and adult incontinence garments, and the like without departing from the scope of the present disclosure.

As used herein, the term "airlaid" refers herein to a web manufactured by an airlaying process In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

As used herein, the term "bonded" refers to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form on fiber. Conjugate fibers are also sometimes referred to as bicomponent or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea" arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al., each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Buten, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10, or 20 gsm to about 120, 125, or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the terms "superabsorbent polymer," "superabsorbent," or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in par on iconicity (a factor of the ionic concentration of the aqueous solution), and the SAP functional polar groups that have an affinity for water. SAP are typically made from the polymerization of acrylic acid blended with sodium hydroxide I the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating or another material or fiber.

Figure 2:
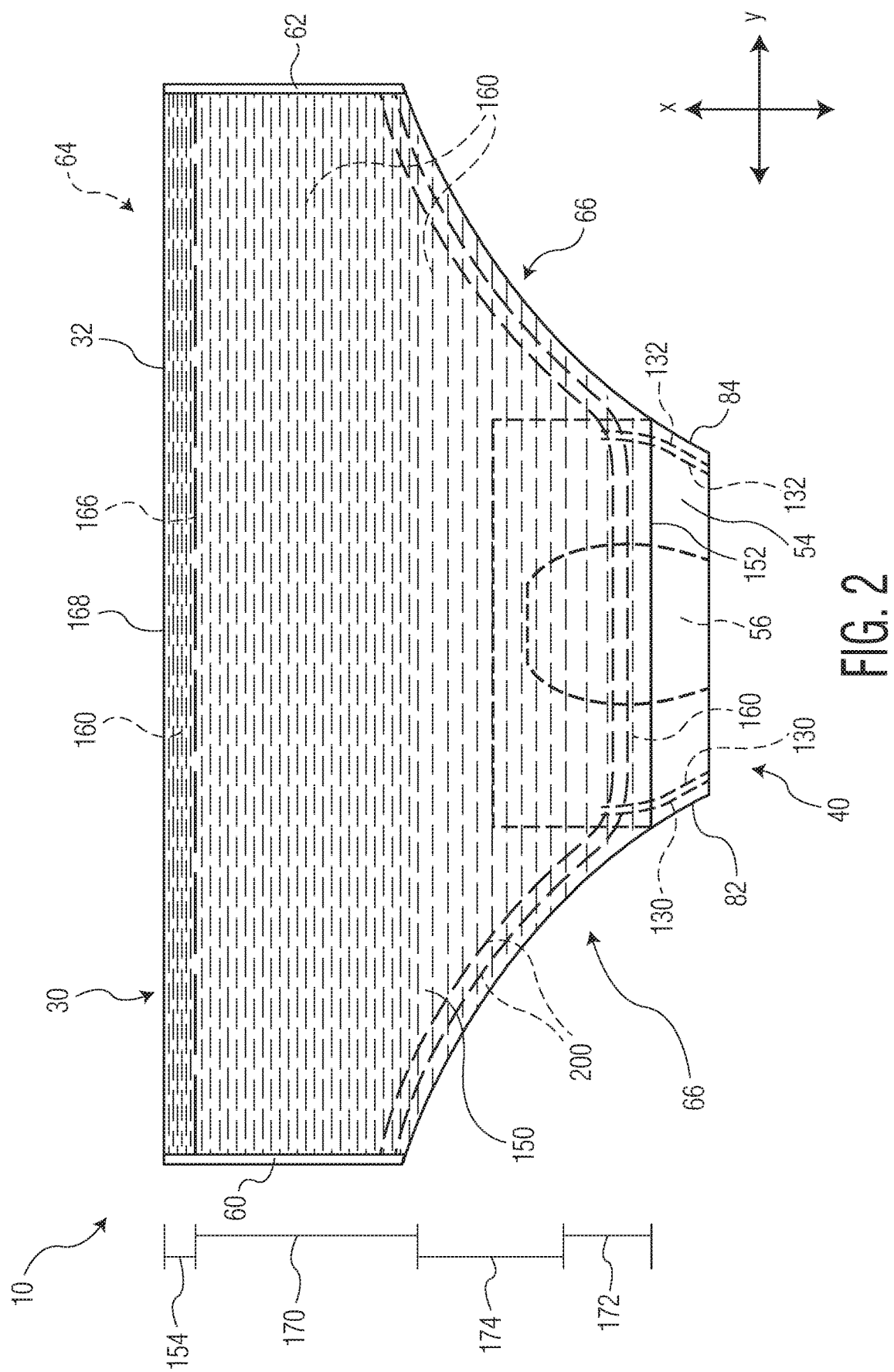
FIG. 2 is an illustration of a back view of the absorbent article of FIG. 1.
Figure 3:
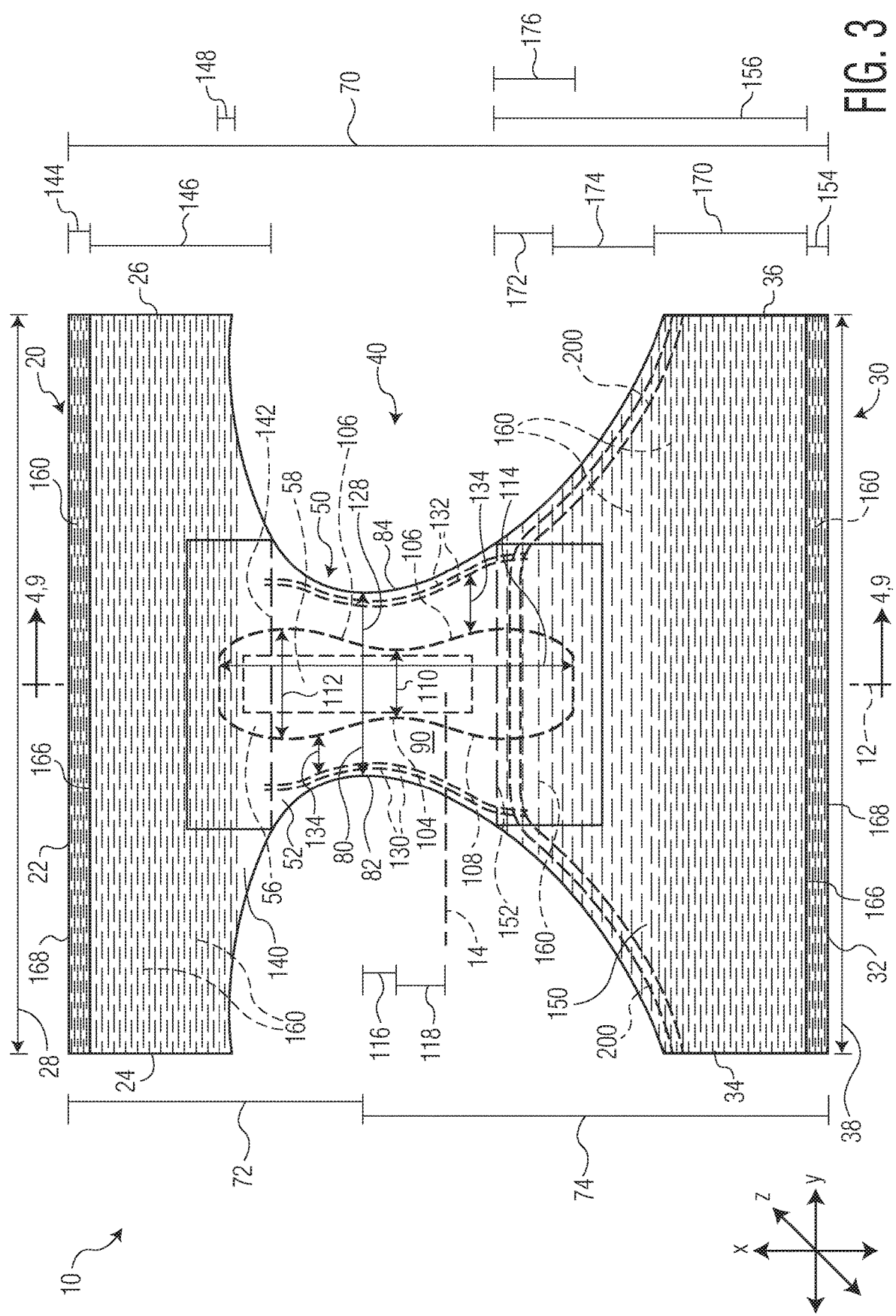
FIG. 3 is an illustration of a plan view of an embodiment of the absorbent article of FIG. 1 in a longitudinally and transversely stretched and laid-flat configuration prior to the joining of the front and back regions with the surface of the absorbent article that faces the wearer when the absorbent article is worn facing the viewer.
Figure 4:
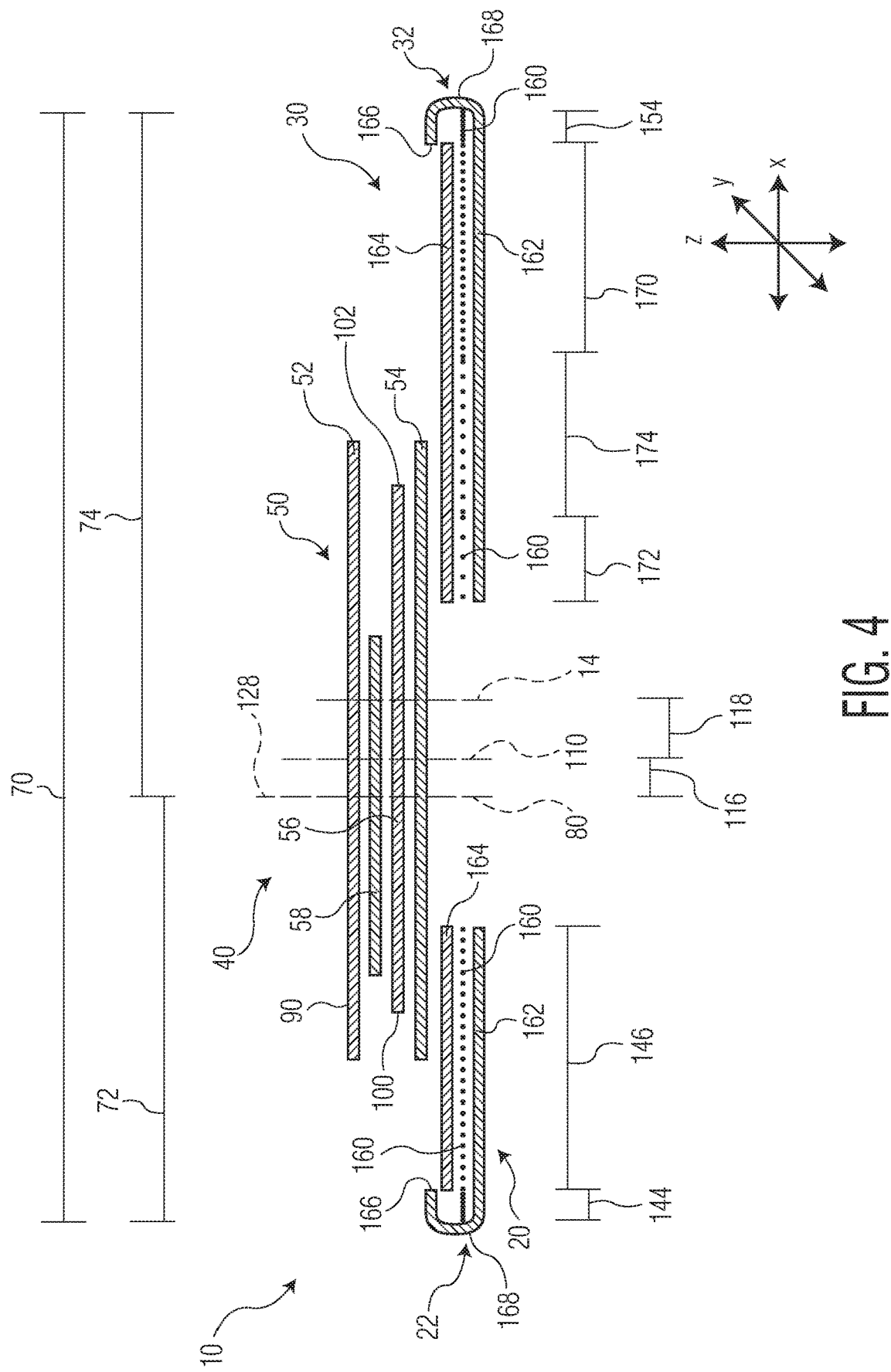
FIG. 4 is an illustration of a cross-sectional view of an embodiment of the absorbent article of FIG. 3 taken along line 4-4.
Figure 5:
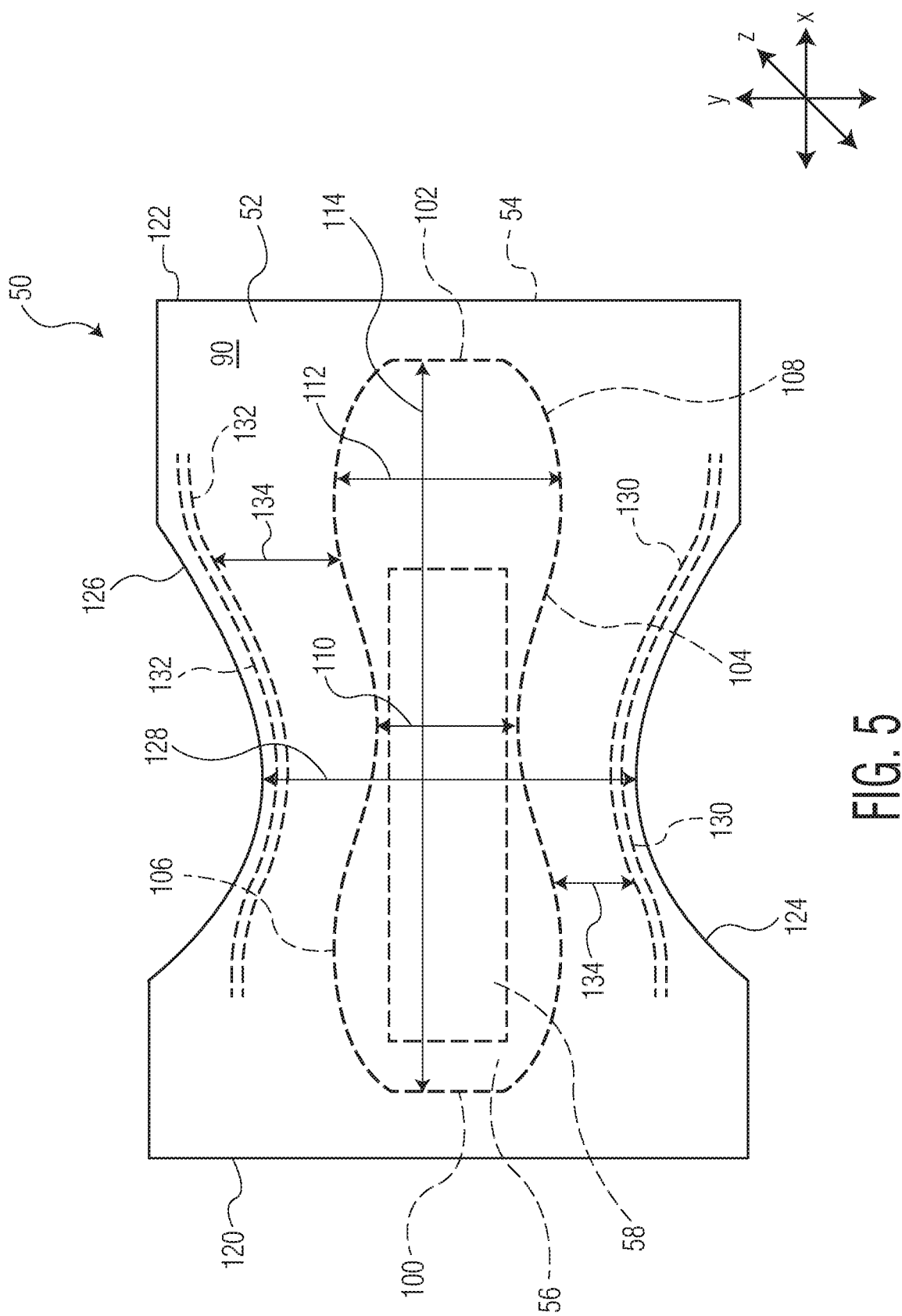
FIG. 5 is an illustration of a plan view of the absorbent assembly of the absorbent article of FIG. 1.

Referring to FIGS. 1-5, an illustration of an exemplary embodiment of an absorbent article 10 is illustrated. FIG. 1 provides an illustration of an embodiment of a front view of the absorbent article 10 in a pull-on, pant-like configuration, FIG. 2 provides an illustration of a back view of the absorbent article 10 of FIG. 1 in a pull-on, pant-like configuration, FIG. 3 provides an illustration of a plan view of an embodiment of the absorbent article 10 of FIG. 1 in a longitudinally and transversely stretched and laid-flat configuration prior to the joining of the front and back regions, 20 and 30, with the surface of the absorbent article 10 that faces the wearer when the absorbent article 10 is worn facing the viewer, FIG. 4 provides an illustration of a cross-sectional view of an embodiment of the absorbent article 10 of FIG. 3 taken along line 4-4, and FIG. 5 provides an illustration of a plan view of the absorbent assembly 50 of the absorbent article 10. Although for illustrative purposes certain features of the present disclosure can be described and illustrated with respect to an adult incontinence garment, the various aspects and embodiments of the present disclosure are also suitable for use with diapers, youth pants, swim pants, training pants, enuresis garments, menstrual pants, and the like.

The absorbent article 10 has a longitudinal direction (X), a transverse direction (Y), and a depth direction (Z). The absorbent article 10 can have a longitudinal axis 12 and a transverse axis 14. The absorbent article 10 is intended to be worn about the lower torso of a human and can have a front region 20, a back region 30, and a crotch region 40 extending between and connecting the front region 20 and the back region 30. The front region 20 and the back region 30 are those regions of the absorbent article 10 that are fitted circumferentially around at least the lower torso of the wearer of the absorbent article 10 including, for example, the wearer's abdomen, lower back, buttock, and hips. The crotch region 40 of the absorbent article 10 is that region of the absorbent article 10 that will be positioned between the wearer's legs when the absorbent article 10 is fitted onto the wearer.

The front region 20 has a front waist edge 22, a first longitudinal direction front side edge 24, and a second longitudinal direction front side edge 26 transversely opposed to the first longitudinal direction front side edge 24. The back region 30 has a back waist edge 32, a first longitudinal direction back side edge 34, and a second longitudinal direction back side edge 36 transversely opposed to the first longitudinal direction back side edge 34. To place the absorbent article 10 into a suitable configuration for wearing about the lower torso of the wearer, the first longitudinal direction front side edge 24 can be bonded to the first longitudinal direction back side edge 34 to form a first side seam 60 and the second longitudinal direction front side edge 26 can be bonded to the second longitudinal direction back side edge 36 to form a second side seam 62. Forming the side seams, 60 and 62, can create a wearable absorbent article 10 having a waist opening 64 and a pair of leg openings 66.

The front region 20 can have a front region width 28 measured in the transverse direction (Y) between the first longitudinal direction front side edge 24 and the second longitudinal direction front side edge 26. The front region width 28 is measured with the absorbent article 10 fully extended in the transverse direction (Y) such as illustrated in FIG. 3 when the absorbent article 10 is in a longitudinally and transversely stretched and laid-flat configuration prior to the joining of the front and back regions to form the side seams, 60 and 62. As used herein, the term "fully extended" describes the condition wherein the absorbent article 10 is extended in a given direction to the point where any further extension in said direction would result in one or more material failures (e.g., rupture or permanent deformation). In embodiments wherein the first longitudinal direction front side edge 24 and the second longitudinal direction front side edge 26 are not parallel with the longitudinal direction (X) (not illustrated), the front region width 28 is the maximum width measured parallel with the transverse direction (Y) from any point on the first longitudinal direction front side edge 24 to any point on the second longitudinal direction front side edge 26. In various embodiments, the front region width 28 may be from 600 or 625 mm to 850 or 900 mm.

The back region 30 can have a back region width 38 measured in the transverse direction (Y) between the first back side edge 34 and the second back side edge 36. The back region width 38 is measured with the absorbent article 10 fully extended in the transverse direction (Y) such as illustrated in FIG. 3 when the absorbent article 10 is in a longitudinally and transversely stretched and laid-flat configuration prior to the joining of the front and back regions to form the side seams, 60 and 62. In embodiments wherein the first back side edge 34 and the second back side edge 36 are not parallel with the longitudinal direction (X) (not illustrated), the back region width 38 is the maximum width measured parallel with the transverse direction (Y) from any point on the first back side edge 34 to any point on the second back side edge 36. In various embodiments, the back region width 38 may be from 600 or 625 mm to 850 or 900 mm.

The absorbent article 10 has an article length 70 as measured in the longitudinal direction (X) from the front waist edge 22 to the back waist edge 32 as illustrated in FIG. 3. The article length 70 is measured with the absorbent article 10 fully extended in the longitudinal direction (X) such as illustrated in FIG. 3 when the absorbent article 10 is in a longitudinally and transversely stretched and laid-flat configuration prior to the joining of the front and back regions to form the side seams, 60 and 62. In various embodiments, the article length 70 may be at least 600, 620, 640, 660, 680, 700, 720, 740, 760, 780, 800, or 820 mm.

The crotch region 40 is disposed in the longitudinal direction (X) between and interconnecting the front region 20 and the back region 30. The absorbent article has an absorbent article narrowest width 80 located within the crotch region 40 of the absorbent article 10. The absorbent article narrowest width 80 is measured in the transverse direction (Y) as the narrowest dimension between a first leg edge 82 and a second leg edge 84 such as illustrated in FIG. 3. The absorbent article narrowest width 80 is measured with the absorbent article 10 in a longitudinally and transversely stretched and laid-flat configuration prior to the joining of the front and back regions to form the side seams, 60 and 62. In various embodiments, the absorbent article narrowest width 80 is less than 25% or 20% of the front region width 28. For example, in various embodiments, the absorbent article narrowest width 80 may be about 150 mm and the front region width 28 may be about 630 mm or 740 mm. In such embodiments, the absorbent article narrowest width 80 may be about 24% or 20% of the front region width 28, respectively. As another example, in various embodiments, the absorbent article narrowest width 80 may be about 150 mm and the front region width 80 may be about 750 mm or 880 mm. In such embodiments, the absorbent article narrowest width 80 may be about 20% or 17% of the front region width 28, respectively. The lower the percentage of the absorbent article narrowest width 80, relative to the front region width 28, the more shaped the absorbent article 10 is within the crotch region 40. In other words, the higher the percentage (up to 100%) the more rectangular the absorbent article 10 is within the crotch region 40. An absorbent article 10 having a more rectangular shape within the crotch region 40 may provide too much bulk of an absorbent article 10 between the wearer's legs which fails to follow the contours of the wearer's legs. This can result in the absorbent article 10 bunching up between the wearer's legs, protruding away from the body of the wearer, and not fitting close to the body of the wearer at the location where body exudate exits the body of the wearer. Providing a non-rectangular shape to the absorbent article 10 within the crotch region 40 of the absorbent article 10 can remove bulk from between the wearer's legs and allow the absorbent article 10 to better fit against and between the contours of the wearer's legs. This can allow for improved conformance of the absorbent article 10 to the body of the wearer.

In various embodiments, the absorbent article narrowest width 80 is positioned between the front waist edge 22 and the transverse axis 14 of the absorbent article 10. In such embodiments, the absorbent article narrowest width 80 is not in an overlapping alignment with the transverse axis 14 of the absorbent article 10. The absorbent article narrowest width 80 can apportion the article length 70 into a first article sub-length 72 and a second article sub-length 74. The first article sub-length 72 can be measured in the longitudinal direction (X) from the front waist edge 22 to the absorbent article narrowest width 80 when the absorbent article 10 is in a longitudinally and transversely stretched and laid-flat configuration prior to the joining of the front and back regions to form the side seams, 60 and 62. The second article sub-length 74 can be measured in the longitudinal direction (X) from the back waist edge 32 to the absorbent article narrowest width 80 when the absorbent article 10 is in a longitudinally and transversely stretched and laid-flat configuration prior to the joining of the front and back regions to form the side seams, 60 and 62. In various embodiments, the first article sub-length 72 is less than the second article sub-length 74. In various embodiments, the first article sub-length 72 can be less than 45% or 40% of the total article length 70. In various embodiments, the second article sub-length 74 can be greater than 55% or 60% of the total article length 70. Wearers of absorbent articles 10 have body shapes in a variety of shapes, sizes, and curvature, and are generally not symmetrical. Placing a symmetrical about the transverse axis 14 absorbent article 10 on a body which is not symmetrical can result in a reduction in proper fit of the absorbent article 10 on the body of the wearer. Positioning the absorbent article narrowest width 80 closer to the front waist edge 22, and not in alignment with the transverse axis 14, can provide for a non-symmetrical about the transverse axis 14 absorbent article 10. As a result, when the absorbent article narrowest width 80 is positioned between the legs of the wearer a greater proportion of the absorbent article 10 is positioned on the posterior side of the wearer's body providing for better coverage of the buttocks of the wearer of the absorbent article 10.

The absorbent article 10 can also include an absorbent assembly 50. The absorbent assembly 50 can extend in the longitudinal direction (X) of the absorbent article 10 from the front region 20, through the crotch region 40, and to the back region 30. In various embodiments, the absorbent assembly 50 can have at least a topsheet layer 52, a backsheet layer 54, and an absorbent core 56 positioned between the topsheet layer 52 and the backsheet layer 54. In various embodiments, the absorbent assembly 50 can have at least a topsheet layer 52, a backsheet layer 54, an absorbent core 56 positioned between the topsheet layer 52 and the backsheet layer 54, and a surge layer 58 positioned between the absorbent core 56 and the topsheet layer 52. The topsheet layer 52 can be bonded to the backsheet layer 54 beyond the outermost edge of the absorbent core 56 to form a perimeter seal for the absorbent assembly 50. The perimeter seal can contain the body exudates within the absorbent assembly 50 of the absorbent article 10.

The topsheet layer 52 defines a body facing surface 90 of the absorbent assembly 50 that may directly contact the body of the wearer and is liquid permeable to receive body exudates. The topsheet layer 52 is desirably provided for comfort and functions to direct body exudates away from the body of the wearer, through its own structure, and towards the absorbent core 56. The topsheet layer 52 desirably retains little to no liquid in its structure, so that it provides a relatively comfortable and non-irritating surface next to the skin of the wearer of the absorbent article 10.

The topsheet layer 52 can be a single layer of material, or alternatively, can be multiple layers that have been laminated together. The topsheet layer 52 can be constructed of any material such as one or more woven sheets, one or more fibrous nonwoven sheets, one or more aperture film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a topsheet layer 52.

In various embodiments the topsheet layer 52 can be constructed from various nonwoven webs such as meltblown webs, spunbond webs, hydroentangled spunlace webs, or through air bonded carded webs. Examples of suitable topsheet layer 52 materials can include, but are not limited to, natural fiber webs (such as cotton), rayon, hydroentangled webs, bonded carded webs of polyester, polypropylene, polyethylene, nylon, or other heat-bondable fibers (such as bicomponent fibers), polyolefins, copolymers of polypropylene and polyethylene, linear low-density polyethylene, and aliphatic esters such as polylactic acid. Finely perforated films and net materials can also be used, as can laminates of/or combinations of these materials. An example of a suitable topsheet layer 52 can be a bonded carded web made of polypropylene and polyethylene such as that obtainable from Sandler Corp., Germany. U.S. Pat. No. 4,801,494 to Datta, et al., and U.S. Pat. No. 4,908,026 to Sukiennik, et al., and WO 2009/062998 to Texol teach various other topsheet materials that may be used as the topsheet layer 52, each of which is hereby incorporated by reference thereto in its entirety. Additional topsheet layer 52 materials can include, but are not limited to, those described in U.S. Pat. No. 4,397,644 to Matthews, et al., U.S. Pat. No. 4,629,643 to Curro, et al., U.S. Pat. No. 5,188,625 to Van Iten, et al., U.S. Pat. No. 5,382,400 to Pike, et al., U.S. Pat. No. 5,533,991 to Kirby, et al., U.S. Pat. No. 6,410,823 to Daley, et al., and U.S. Publication No. 2012/0289917 to Abuto, et al., each of which is hereby incorporated by reference thereto in its entirety.

In various embodiments, the topsheet layer 52 may contain a plurality of apertures formed therethrough to permit body exudates to pass more readily into the absorbent core 56. The apertures may be randomly or uniformly arranged throughout the topsheet layer 52. The size, shape, diameter, and number of apertures may be varied to suit an absorbent article's 10 particular needs.

In various embodiments, the tosphheet layer 52 can have a basis weight ranging from about 5, 10, 15, 20, or 25 gsm to about 50, 100, 120, 125, or 150 gsm. For example, in an embodiment, a topsheet layer 52 can be constructed from a through air bonded carded web having a basis weight ranging from about 15 gsm to about 100 gsm. In another example, a topsheet layer 52 can be constructed from a through air bonded carded web having a basis weight from about 20 gsm to about 50 gsm, such as a through air bonded carded web that is readily available from nonwoven material manufacturers, such as Xiamen Yanjan Industry, Beijing, DaYuan Nonwoven Fabrics, and others.

In various embodiments, the topsheet layer 52 can be at least partially hydrophilic. In various embodiments, a portion of the topsheet layer 52 can be hydrophilic and a portion of the topsheet layer 52 can be hydrophobic. In various embodiments, the portions of the topsheet layer 52 which can be hydrophobic can be either an inherently hydrophobic material or can be a material treated with a hydrophobic coating.

In various embodiments, the topsheet layer 52 can be a multicomponent topsheet layer 52 such as by having two or more different nonwoven or film materials, with the different materials placed in separate locations in the transverse direction (Y) of the absorbent assembly 50. For example, the topsheet layer 52 can be a two layer or multicomponent material having a central portion positioned along and straddling a longitudinal axis 12 of an absorbent article 10, with lateral side portions flanking and bonded to each side edge of the central portion. The central portion can be constructed from a first material and the side portions can be constructed from a material which can be the same as or different from the material of the central portion. In such embodiments, the central portion may be at least partially hydrophilic and the side portions may be inherently hydrophobic or may be treated with a hydrophobic coating. Examples of constructions of multi-component topsheet layers are generally described in U.S. Pat. No. 5,961,505 to Coe, U.S. Pat. No. 5,415,640 to Kirby, and U.S. Pat. No. 6,117,523 to Sugahara, each of which is incorporated herein by reference thereto in its entirety.

In various embodiments, a central portion of a topsheet layer 52 can be positioned symmetrically about the absorbent article 10 longitudinal axis 12. Such central longitudinally directed central portion can be a through air bonded carded web ("TABCW") having a basis weight between about 15 and about 100 gsm. Previously described nonwoven, woven, and aperture film topsheet layer materials may also be used as the central portion of a topsheet layer 52. In various embodiments, the central portion can be constructed from a TABCW material having a basis weight from about 20 gsm to about 50 gsm such as is available from Xiamen Yanjan Industry, Beijing, DaYuan Nonwoven Fabrics, and others. Alternatively, aperture films, such as those available from such film suppliers as Texol, Italy and Tredegar, U.S.A. may be utilized. Different nonwoven, woven, or film sheet materials may be utilized as the side portions of the topsheet layer 52. The selection of such topsheet layer 52 materials can vary based upon the overall desired attributes of the topsheet layer 52. For example, it may be desired to have a hydrophilic material in the central portion and hydrophobic-barrier type materials in the side portions to prevent leakage and increase a sense of dryness in the area of the side portions. Such side portions can be adhesively, thermally, ultrasonically, or otherwise bonded to the central portion along or adjacent the longitudinally directed side edges of the central portion. Traditional absorbent article construction adhesive may be used to bond the side portions to the central portion. Either of the central portion and/or the side portions may be treated with surfactants and/or skin-health benefit agents, as are well known in the art.

Such longitudinally directed side portions can be of a single or multi-layered construction. In various embodiments, the side portions can be adhesively or otherwise bonded laminates. In various embodiments, the side portions can be constructed of an upper fibrous nonwoven layer, such as a spunbond material, laminated to a bottom layer of a hydrophobic barrier film material. Such a spunbond layer may be formed from a polyolefin, such as a polypropylene and can include a wetting agent if desired. In various embodiments, a spunbond layer can have a basis weight from about 10 or 12 gsm to about 30 or 70 gsm and can be treated with hydrophilic wetting agents. In various embodiments, a film layer may have apertures to allow fluid to permeate to lower layers, and may be either of a single layer or multi-layer construction. In various embodiments, such film can be a polyolefin, such as polyethylene having a basis weight from about 10 to about 40 gsm. Construction adhesive can be utilized to laminate the spunbond layer to the film layer at an add-on level of between about 0.1 gsm and 15 gsm. When a film barrier layer is used in the overall topsheet layer 52 design, it may include opacifying agents, such as film pigments, that can help the film in masking stains along the absorbent article 10 side edges, thereby serving as a masking element. In such a fashion, the film layer can serve to limit visualization of a fluid insult stain along the absorbent assembly 50 side edges when viewed from above the topsheet layer 52. The film layer may also serve as a barrier layer to prevent rewet of the topsheet layer 52 as well as to prevent the flow of fluid off the side edges of the absorbent assembly 50. In various embodiments, the side portions can be laminates such as a spunbond-meltblown-meltblown-spunbond layer ("SM MS") laminate, spunbond-film laminate, or alternatively, other nonwoven laminate combinations.

The backsheet layer 54 of the absorbent assembly 50 is generally liquid impermeable and is the portion of the absorbent assembly 50 which faces the garments of the wearer. The backsheet layer 54 can permit the passage of air or vapor out of the absorbent article 10 while still blocking the passage of liquids. Any liquid impermeable material may generally be utilized to form the backsheet layer 54. The backsheet layer 54 can be composed of a single layer or multiple layers, and these one or more layers can themselves comprise similar or different materials. Suitable material that may be utilized can be a microporous polymeric film, such as a polyolefin film or polyethylene or polypropylene, nonwovens, and nonwoven laminates, and film/nonwoven laminates. The particular structure and composition of the backsheet layer 54 can be selected from various known films and/or fabrics with the particular material being selected as appropriate to provide the desired level of liquid barrier, strength, abrasion resistance, tactile properties, aesthetics, and so forth. In various embodiments, a polyethylene film can be utilized that can have a thickness in the range of from about 0.2 or 0.5 mils to about 3.0 or 5.0 mils. An example of a backsheet layer 54 can be a polyethylene film such as that obtainable from Pliant Corp., Schaumburg, IL, USA. Another example can include calcium carbonate-filled polypropylene film. In still another embodiment, the backsheet layer 54 can be a hydrophobic nonwoven material with water barrier properties such as a nonwoven laminate, an example of which can be a spunbond, meltblown, meltblown, spunbons, four-layered laminate.

In various embodiments, the backsheet layer 54 can be a two layer construction, including an outer layer material and an inner layer material which can be bonded together. The outer layer can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer can be a 20 gsm spunbond polypropylene non-woven web. The inner layer can be either vapor permeable (i.e., "breathable") or vapor impermeable. The inner layer may be manufactured from a thin plastic film, although other liquid impermeable materials may also be used. The inner layer can inhibit liquid body exudates from leaking out of the absorbent assembly 50 and wetting articles, such as bed sheets and clothing, as well as the wearer and caregiver. An example of a material for an inner layer can be a printed 19 gsm Berry Plastics XP-8695H film or equivalent commercially available from Berry Plastics Corporation, Evansville, IN, U.S.A.

The backsheet layer 54 can, therefore, be of a single or multiple layer construction, such as of multiple film layers or laminates of film and nonwoven fibrous layers. Suitable backsheet layers 206 can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and U.S. Pat. No. 6,376,095 to Cheung, et al., each of which are hereby incorporated by reference thereto in its entirety.

An absorbent core 56 can be positioned between the topsheet layer 52 and the backsheet layer 54 of the absorbent article 10. In various embodiments, the absorbent core 56 can extend in the longitudinal direction (X) of the absorbent assembly 50. The absorbent core 56 can have a first portion located in the crotch region 40 of the absorbent article 10. In various embodiments, the absorbent core 56 can have a second portion located in a portion of at least one of the front region 20 or the back region 30. In various embodiments, the absorbent core 56 can have a first portion located within the crotch region 40 and a second portion located in a portion of the front region 20. In various embodiments, the absorbent core 56 can have a first portion located within the crotch region 40 and a second portion located in a portion of the back region 30. In various embodiments, an absorbent core 56 can have a first portion located within the crotch region 40, a second portion located in a portion of the front region 20, and a third portion located in a portion of the back region 30.

The absorbent core 56 can generally be any single layer structure or combination of layer components, which can demonstrate some level of compressibility, conformability, be non-irritating to the wearer's skin, and capable of absorbing and retaining liquids and other body exudates. In various embodiments, the absorbent core 56 can be formed from a variety of different materials and can contain any number of desired layers. For example, the absorbent core 56 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of wood pulp fluff can be identified with the trade designation NB416, available from Weyerhaeuser Corp., and is a bleached, highly absorbent wood pulp containing primarily soft wood fibers.

In various embodiments, if desired, the absorbent core 56 can include an optional amount of superabsorbent material. Examples of suitable superabsorbent material can include poly(acrylic acid), poly(methacrylic acid), poly(acrylamide), poly(vinyl ether), maleic anhydride copolymers with vinyl ethers and a-olefins, poly(vinyl pyrrolidone), poly(vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent core 56 in any amount as desired.

Regardless of the combination of absorbent materials used in the absorbent core 56, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

The absorbent core 56 can have a perimeter edge 108 formed by a first transverse direction end edge 100, a second transverse direction end edge 102 opposed to the first transverse direction end edge 100, and a pair of opposing longitudinal direction side edges, 104 and 106, extending between and connecting the first transverse direction end edge 100 and the second transverse direction end edge 102. The perimeter edge 108 of the absorbent core 56 defines the overall shape of the absorbent core 56. In various embodiments, the perimeter edge 108 defines a shape of an absorbent core 56 which is non-rectangular.

The longitudinal direction side edges, 104 and 106, of the absorbent core 56 can be non-linear so as to provide the absorbent core 56 with an absorbent core narrowest width 110 and an absorbent core maximum width 112. The absorbent core narrowest width 110 is measured in the transverse direction (Y) at the narrowest point between the longitudinal direction side edges, 104 and 106, of the absorbent core 56. In various embodiments, the absorbent core narrowest width 110 can be less than 65 or 75 mm. The absorbent core maximum width 112 is measured in the transverse direction (Y) at the greatest distance between the longitudinal direction side edges, 104 and 106, of the absorbent core 56. In various embodiments, the absorbent core maximum width is from 90 or 95 mm to 100, 110, 130, 140, 150, 200, or 210 mm. In various embodiments, the absorbent core narrowest width 110 is less than 85, 80, 75, 70, 65, 60, 55, 50, or 45% of the absorbent core maximum width 112. For example, in various embodiments, the absorbent core narrowest width 110 may be 62 mm and the absorbent core maximum width may be 96 mm such that the absorbent core narrowest width 110 is about 65% of the absorbent core maximum width 112. For example, in various embodiments, the absorbent core narrowest width 110 may be 75 mm and the absorbent core maximum width 112 may be 110 mm such that the absorbent core narrowest width 110 is about 68% of the absorbent core maximum width 112. For example, in various embodiments, the absorbent core narrowest width 110 may be 75 mm and the absorbent core maximum width 112 may be 150 mm such that the absorbent core narrowest width 110 is about 50% of the absorbent core maximum width 112. An absorbent core 56 having a more rectangular shape within the crotch region 40 may provide too much bulk of an absorbent article 10 between the wearer's legs which fails to follow the contours of the wearer's legs. This can result in the absorbent article 10 bunching up between the wearer's legs, protruding away from the body of the wearer, and not fitting close to the body of the wearer at the location where body exudate exits the body of the wearer. Providing a non-rectangular shape to the absorbent core 56 within the crotch region 40 of the absorbent article 10 can remove bulk from between the wearer's legs and allow the absorbent article 10 to better fit against and between the contours of the wearer's legs. This can allow for improved conformance of the absorbent article 10 to the body of the wearer.

The absorbent core narrowest width 110 can be less than 12, 10, 9, or 8% of the front region width 28. For example, in various embodiments, the absorbent core narrowest width 110 may be 62 mm and the front region width 28 may be 630 mm or 740 mm. In such embodiments, the absorbent core narrowest width 110 can be about 10% or 8%, respectively, of the front region width 28. As another example, in various embodiments, the absorbent core narrowest width 110 may be 62 mm and the front region width 28 may be about 750 mm or 880 mm. In such embodiments, the absorbent core narrowest width 110 can be about 8% or 7%, respectively, of the front region width 28.

The absorbent core maximum width 112 can be less than 25, 23, 20, 16, 13, or 11% of the front region width 28. For example, in various embodiments, the absorbent more maximum width can be 96 mm and the front region width 28 can be 630 mm or 740 mm. In such embodiments, the absorbent core maximum width 112 can be about 15% or 13%, respectively, of the front region width 28. As another example, in various embodiments, the absorbent core maximum width 112 can be 96 mm and the front region width 28 can be about 750 mm or 880 mm. In such embodiments, the absorbent core maximum width 112 can be about 13% or 11%, respectively, of the front region width 28. As another example, the absorbent core maximum width 112 can be 210 mm and the front region width 28 can be about 900 mm. In such embodiments, the absorbent core maximum width 112 can be about 23% of the front region width 28.

The absorbent core narrowest width 110 is positioned within the crotch region 40 of the absorbent article 10 and between the absorbent article narrowest width 80 and the transverse axis 14 of the absorbent article 10. The absorbent core narrowest width 110, therefore, does not coincide with either the absorbent article narrowest width 80 or the transverse axis 14 of the absorbent article 10. In various embodiments, the absorbent core narrowest width 110 is offset from the absorbent article narrowest width 80 by a distance 116 in the longitudinal direction (X) of at least 10, 12, 14, 16, 18, 20, 22, 24, 26, 28, or 30 mm. In various embodiments, the absorbent core narrowest width 110 is offset from the absorbent article narrowest width 80 by a distance 116 in the longitudinal direction (X) from about 10, 12, 14, 16, or 18 mm, to about 20, 22, 24, 26, 28, or 30 mm. In various embodiments, the absorbent core narrowest width 110 is offset from the absorbent article narrowest width 80 by a distance 116 in the longitudinal direction (X) of at least 1% of the absorbent article 10 total article length 70. In various embodiments, the absorbent core narrowest width 110 is offset from the absorbent article narrowest width 80 by a distance 116 in the longitudinal direction (X) from about 1 or 2% to about 4 or 5% of the absorbent article 10 total article length 70. In various embodiments, the absorbent core narrowest width 110 is offset from the transverse axis 14 of the absorbent article 10 by a distance 118 in the longitudinal direction (X) of at least 50, 52, 54, 56, 58, 60, 62, 64, 66, 68, 70, 72, 74, or 76 mm. In various embodiments, the absorbent core narrowest width 110 is offset from the transverse axis 14 of the absorbent article 10 by a distance 118 in the longitudinal direction (X) from about 50, 52, 54, 56, 58, 60, or 62 mm to about 64, 66, 68, 70, 72, 74, or 76 mm. In various embodiments, the absorbent core narrowest width 110 is offset from the transverse axis 14 of the absorbent article 10 by a distance 118 in the longitudinal direction (X) of from about 6 or 8% to about 9 or 15% of the absorbent article 10 total article length length 70. As described herein, an absorbent article 10 having a more rectangular shape within the crotch region 40 may provide too much absorbent article bulk between the legs of the wearer of the absorbent article 10 which can result in the absorbent article bunching up between the wearer's legs, protruding away from the body of the wearer and not fitting close to the body of the wearer. Additionally, wearers of absorbent articles have body shapes which are a variety of shapes, sizes, and curvature, and generally not symmetrical. Positioning, the absorbent article narrowest width 80 closer to the front waist edge 22 can provide for a non-symmetrical absorbent article 10 wherein a greater proportion of the absorbent article 10 is positioned on the posterior side of the wearer's body providing for better coverage of the buttocks of the wearer of the absorbent article 10 and a lesser proportion of the absorbent article 10 is positioned on the anterior side of the wearer's body providing for a reduction of friction between the material of the absorbent article 10 and the wearer's legs when they move. Positioning the absorbent core narrowest width 110 between the absorbent article narrowest width 80 and the transverse axis 14 can place the absorbent core 56 where it is needed most for capture of body exudate released from the wearer of the absorbent article 10 and minimize the bulkiness of the material of the absorbent core 56 between the legs of the wearer of the absorbent article 10.

The absorbent core 56 can have an absorbent core length 114 measured in the longitudinal direction (X) of the absorbent article 10. The absorbent core length 114 is measured as the maximum distance between the first transverse direction end edge 100 of the absorbent core 56 and the second transverse direction end edge 102 of the absorbent core 56. As described herein, the total article length 70 of the absorbent article 10 can be from 600 mm to 820 mm. In various embodiments, the absorbent core length 114 can be less than 50%, 45%, or 40% of the absorbent article 10 total article length 70. For example, in various embodiments, the absorbent core length 114 can be 300 mm and the absorbent article 10 total article length 70 can be 646 mm. In such embodiments, the absorbent core length 114 can be 46% of the total article length 70. As another example, in various embodiments, the absorbent core length 114 can be 300 mm and the total article length 70 can be 712 mm. In such embodiments, the absorbent core length 114 can be 42% of the total article length 70. As another example, in various embodiments, the absorbent core length 114 can be 300 mm and the total article length 70 can be 765 mm. In such embodiments, the absorbent core length 114 can be 39% of the total article length 70.

By way of example, suitable materials and/or structures for the absorbent core 56 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al. each of which is hereby incorporated by reference thereto in its entirety.

In various embodiments, an absorbent core 56 can be a single layer structure and can include, for example, a matrix of cellulosic fluff and superabsorbent material. In various embodiments, an absorbent core 56 can have at least two layers of material, such as, for example, a body facing layer and a garment facing layer. In various embodiments, the two layers can be identical to each other. In various embodiments, the two layers can be different from each other. In such embodiments, the two layers can provide the absorbent article 10 with different absorption properties as deemed suitable. In various embodiments, the body facing layer of the absorbent core 56 may be constructed of an airlaid material and the garment facing layer of the absorbent core 56 may be constructed of a superabsorbent polymer-containing compressed sheet. In such embodiments, the airlaid material can have a basis weight from about 40 to about 200 gsm and the superabsorbent polymer-containing compressed sheet can be a cellulosic fluff based material that can be a combination of cellulosic pulp and SAP enclosed with a tissue carrier and having a basis weight from about 40 to about 400 gsm.

In various embodiments, the absorbent assembly 50 can include a surge layer 58 positioned between the absorbent core 56 and the topsheet layer 52. The surge layer 58 can be adapted to work with the absorbent core 56 in absorbing body exudates. In various embodiments, the surge layer 58 can have a higher void volume that the absorbent core 56 to quickly intake and hold body exudates so that the absorbent core 56 has time to absorb the body exudates without such body exudates leaking from the absorbent article 10. The surge layer 58 can take on any size and shape as desired and as deemed suitable. For example, in FIGS. 3 and 5, the surge layer 58 is illustrated in the shape of a rectangle and has a size dimension smaller than the absorbent core 56.

The absorbent assembly 50 can have a first transverse direction end edge 120, a second transverse direction end edge 122 opposed to the first transverse direction end edge 120, and a pair of opposing longitudinal direction side edges, 124 and 126, extending between and connecting the first transverse direction end edge 120 and the second transverse direction end edge 122.

In various embodiments, at least portions of the longitudinal direction side edges, 124 and 126, can be non-linear so as to provide the absorbent assembly 50 with a non-rectangular shape. A non-rectangular shape can provide the absorbent assembly 50 with an absorbent assembly narrowest width 128 which is measured in the transverse direction (Y) at the narrowest point between the longitudinal direction side edges, 124 and 126. The absorbent assembly narrowest width 128 is measured with the absorbent assembly 50 in a longitudinally and transversely stretched and laid-flat configuration.

In various embodiments, the absorbent assembly narrowest width 128 is less than 25% or 20% of the front region width 28. For example, in various embodiments, the absorbent assembly narrowest width 128 may be about 150 mm and the front region width 28 may be about 630 mm or 740 mm. In such embodiments the absorbent assembly narrowest width 128 may be about 24% or 20% of the front region width, respectively. As another example, in various embodiments, the absorbent assembly narrowest width 128 may be about 150 mm and the front region width 28 may be about 750 mm or 880 mm. In such embodiments, the absorbent assembly narrowest width 128 may be about 20% or 17% of the front region width 28, respectively. The lower the percentage of the absorbent assembly narrowest width 128, relative to the front region width 28, the more shaped the absorbent assembly 50. In other words, the higher the percentage (up to 100%) the more rectangular the absorbent assembly 50.

In various embodiments, the absorbent core narrowest width 110 can be less than 50% or 45% of the absorbent assembly narrowest width 128. For example, in various embodiments, the absorbent core narrowest width 110 can be 62 mm and the absorbent assembly narrowest width 128 can be 150 mm. In such embodiments, the absorbent core narrowest width 110 can be 41% of the absorbent assembly narrowest width 128.

In various embodiments, such as illustrated in FIGS. 1-5, the non-linear portions of the longitudinal direction side edges, 124 and 126, of the absorbent assembly 50 can be arcuate and can form portions of the first leg side edge 82 and the second leg side edge 84 of the absorbent article 10. In such embodiments, the absorbent assembly narrowest width 128 is identical to the absorbent article narrowest width 80. In such embodiments, the absorbent core narrowest width 110 can be less than 50% or 45% of the absorbent article narrowest width 80.

The absorbent article 10 can have a first longitudinally extending elastic material 130 located in the crotch region 40 of the absorbent article 10 and positioned between the first longitudinal direction side edge 104 of the absorbent core 56 and the first leg side edge 82 of the absorbent article 10. The absorbent article can have a second longitudinally extending elastic material 132 located in the crotch region 40 of the absorbent article 10 and positioned between the second longitudinal direction side edge 106 of the absorbent core 56 and the second leg side edge 84 of the absorbent article 10. Each elastic material, 130 and 132, can be an elastic strand, ribbon, or strip of elastic material. For example, each of the Figures illustrates a pair of elastic strands forming the elastic material 130 extending longitudinally between the first longitudinal direction side edge 104 of the absorbent core 56 and the first leg side edge 82 of the absorbent article 10 and a pair of elastic strands forming the elastic material 132 extending longitudinally between the second longitudinal direction side edge 106 of the absorbent core 56 and the second leg side edge 84 of the absorbent article 10.

Figure 6:
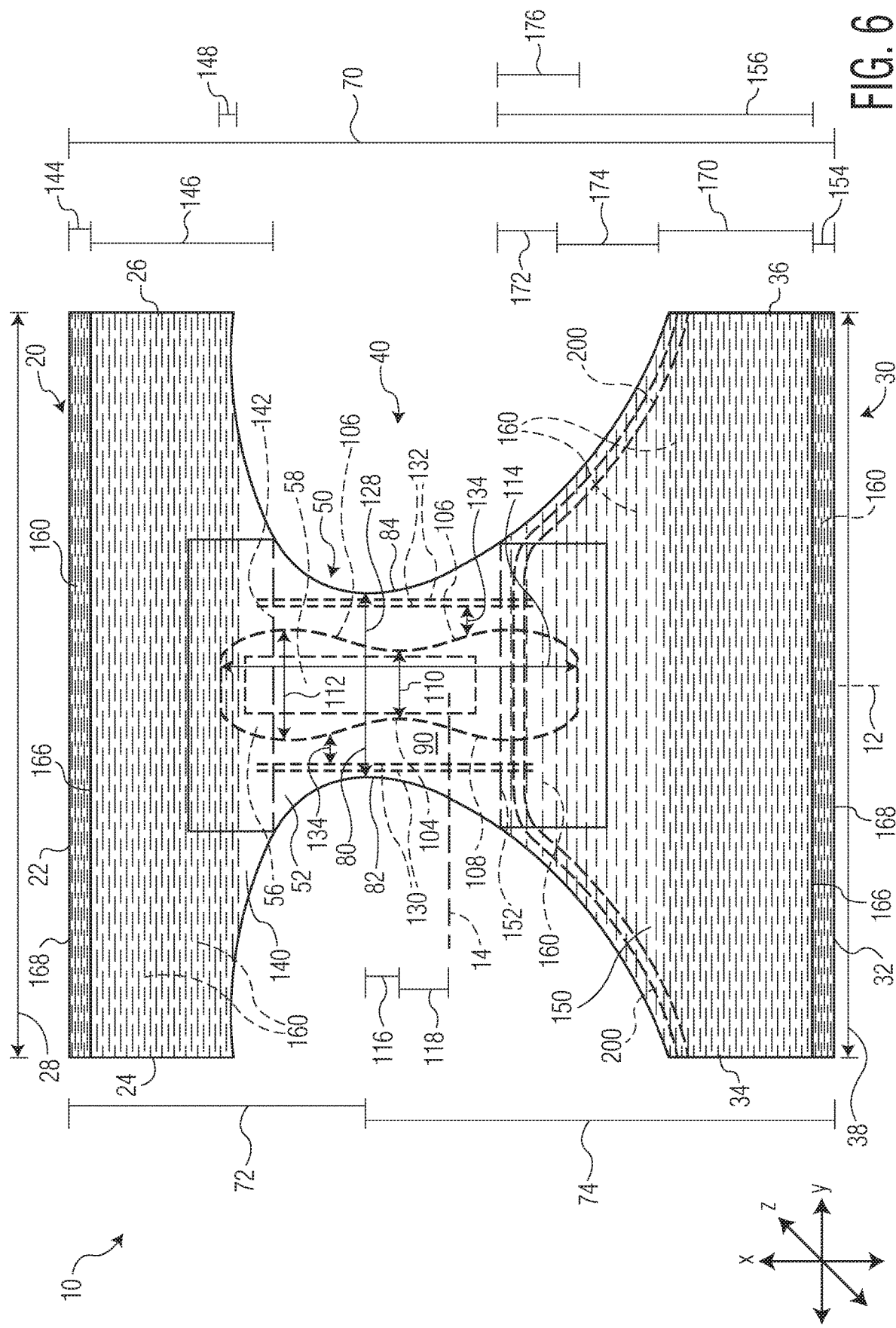
FIG. 6 is an illustration of a plan view of an alternate embodiment of the absorbent article of FIG. 1 in a longitudinally and transverse stretched and laid-flat configuration prior to the joining of the front and back regions with the surface of the absorbent article that faces the wearer when the absorbent article is worn facing the viewer.

Each of the longitudinally extending elastic materials, 130 and 132, can have an interior perimeter which is the portion of the elastic materials, 130 and 132, closest to the absorbent core 56 without coming into a configuration such that it will overlay the absorbent core 56. The interior perimeter of each of the longitudinally extending elastic materials, 130 and 132, can be positioned at a spatial distance 134 from the longitudinal direction side edges, 104 and 106, of the absorbent core 56. The spatial distance 134 of each of the longitudinally extending elastic materials, 130 and 132, from each of the longitudinal direction side edges, 104 and 106, at the locations of each of the absorbent article narrowest width 80, absorbent core narrowest width 110, and the transverse axis 14 can be a minimum of 15 mm. In various embodiments, the spatial distance 134 at each of the locations of the absorbent article narrowest width 80, the absorbent core narrowest width 110, and the transverse axis 14 can be from about 15, 17, 19, or 21 mm to about 23, 25, 27, 29, or 31 mm. In various embodiments, the spatial distance 134 at each of the locations of the absorbent article narrowest width 80, the absorbent core narrowest width 110, and the transverse axis 14 can be a minimum of 1.5, 2, 2.5, 3, 3.5, 4, 4.5, 5, or 5.5% of the front region width 28. In various embodiments, the spatial distance 134 can be uniform. In various embodiments, the spatial distance 134 can be non-uniform. Such a spatial distance 134 can allow for movement of the absorbent core 56 as the wearer moves their body. The spatial distance 134 can isolate the absorbent core 56 of the absorbent article 10 such that when the wearer of the absorbent article 10 moves their body and/or legs, the absorbent core 56 is not impacted by such movement of the wearer. If the longitudinally extending elastic materials, 130 and 132, were not separated by a minimum spatial distance 134 from the absorbent core 56, the movement of the wearer could cause the elastic materials, 130 and 132, to pull and twist the absorbent core 56 which can lead to movement of the absorbent core 56 out of proper placement for capturing body exudates. In various embodiments, the longitudinally extending elastic materials, 130 and 132, can be non-linear, such as, for example, illustrated in FIGS. 1-4. In various embodiments, the longitudinally extending elastic strands, 130 and 132, can be linear, such as, for example, illustrated in FIG. 6.

As illustrated in FIGS. 1-4, the front region 20 of the absorbent article 10 can be constructed of an elastomeric panel 140. The elastomeric panel 140 of the front region 20 can be bordered by a front lower edge 142, the first front side edge 24, the second front side edge 26, and the front waist edge 22. The back region 30 can be constructed of an elastomeric panel 150. The elastomeric panel 150 of the back region 30 can be bordered by a back lower edge 152, the first back side edge 34, the second back side edge 36, and the back waist edge 32. The elastomeric panels, 140 and 150, can have elastic material such that the elastomeric panels, 140 and/or 150, upon application of a stretching force, is stretchable in the transverse direction (Y), and which upon release of the stretching force, contracts/returns at least a portion of its stretched length, desirably to its original dimension.

In various embodiments, the elastic material in each of the elastomeric panels, 140 and 150, can be elastomeric strands of material such as can be preformed from LYCRA brand fibers/yarns for example. LYCRA is a registered trademark of E.I. DuPont DeNemours Co., Wilmington, DE, U.S.A. The elastomeric strands can have a round, semi-circular, square, rectangular, oval, or other geometrical configuration. In various embodiments, the elastic material can be an elastomeric polymeric film layer. In various embodiments, a suitable elastomeric polymeric film layer can be a stretch-bonded laminate (SBL) in which an elastic core or middle layer is elongated before two opposing outer nonwoven web layers are bonded thereto. Another suitable material for the elastomeric polymeric film layer is a necked bonded laminate (NBL). The NBL material is a three layer laminate but the elastic core or middle layer is not pre-stretched prior to being attached to the two outer nonwoven web layers. Instead, the opposing outer nonwoven web layers are necked stretched before the elastic core or middle layer is bonded to them. Other examples of such elastomeric materials that can be used as an elastomeric polymeric film layer include a continuous filament stretch bonded laminate (CFSBL), a vertical filament laminate (VFL), a necked stretch bonded laminate (NSBL), or a necked thermal laminate (NTL). Combinations of such materials can also be used. Such materials are described in U.S. Pat. No. 4,720,415 to Vander Wielen et al., U.S. Pat. No. 5,366,793 to Fitts, et al., U.S. Pat. No. 5,385,775, to Wright, U.S. Pat. No. 6,969,441 to Welch et al., U.S. Pat. No. 6,978,486 to Zhou et al., U.S. Pat. No. 7,803,244 to Siqueira et al., and U.S. Pat. No. 5,226,992 to Morman et al., each of which are hereby incorporated by reference thereto in its entirety. The elastomeric laminates just described will typically include an elastomeric layer and at least one surface-bonded nonwoven web layer such as a meltblown, spunbond, or through-air bonded web.

To form each of the elastomeric panels, 140 and 150, the elastic material within the elastomeric panels, 140 and 150, can be sandwiched between a single nonwoven material which has been folded over onto itself or can be sandwiched between two separate nonwoven materials. The elastic materials can be sandwiched and held between the nonwoven layers with adhesive, ultrasonic bonding, heat pressure sealing, or any other means deemed suitable. The elastic material within the elastomeric panel 140 of the front region 20 can extend continuously between the first front side edge 24 and the second front side edge 26 of the front region 20. The elastic material within the elastomeric panel 150 of the back region 30 can extend continuously between the first back side edge 34 and the second back side edge 36. Continuous extension of the elastic material in the transverse direction (Y) in each of the front region 20 and the back region 30 can provide for continuous tension of the elastic material in the transverse direction (Y) in the front region 20 and the back region 30. In other words, the elastic material in each of the front region 20 and the back region 30 remains active and capable of stretching/retracting continuously in the transverse direction (Y) throughout the length of the elastic material in the transverse direction (Y) of the absorbent article 10.

Each of the elastomeric panels, 140 and 150, can have a first portion, 144 and 154, respectively, which can be the waist portion of the absorbent article 10. In various embodiments, each first portion, 144 and 154, of the elastomeric panels, 140 and 150, respectively, can have a length in the longitudinal direction (X) which is less than about 5, 4, or 3% of the absorbent article length 70. In the illustrative and exemplary embodiments of FIGS. 1-4, the first portion, 144 and 154, can be further illustrated as the elastic material 160 sandwiched between the first nonwoven layer 162 which has been folded over onto itself creating a fold 168 and placing a material edge 166 on the interior of the absorbent article 10. In various embodiments, the elastic material in each of the first portions, 144 and 154, of the elastomeric panels, 140 and 150, can have a uniform tension in the transverse direction (Y) and in the longitudinal direction (X).

Each of the elastomeric panels, 140 and 150, can have a second portion, 146 and 156, respectively, which can be the chassis portion of the absorbent article 10. The second portion, 146 and 156, of each of the elastomeric panels, 140 and 150, respectively, can exclude the first portions, 144 and 154, and can extend in the longitudinal direction (X) from the first portions, 144 and 154, towards the crotch region 40 of the absorbent article 10. As described herein, in various embodiments, the absorbent core 56 can have a first portion in the crotch region 40 of the absorbent article 10 and a second portion located in a portion of at least one of the front region 20 or the back region 30. In such embodiments, the second portion of the absorbent core 56 located in a portion of at least one of the front region 20 or the back region 30 can be in an overlapping configuration with a portion of the elastic material in the respective second portions, 146 and/or 156, of the front region 20 and/or the back region 30. In various embodiments, the absorbent core 56 can have a first portion located in the crotch region 40, a second portion located in a portion of the second portion 146 of the front region 20, and a third portion located in a portion of the second portion 156 of the back region 30. In such embodiments, the second portion of the absorbent core 56 located in the second portion 146 of the front region 20 can be in an overlapping configuration with a portion of the elastic material in the second portion 146 of the front region 20 and the third portion of the absorbent core 56 located in the second portion 156 of the back region 40 can be in an overlapping configuration with a portion of the elastic material in the second portion 156 of the back region 40. As the absorbent core 56 has a thickness dimension in the depth direction (Z) of the absorbent article 10, the overlapping configuration may result in a non-uniform tension of the elastic material in the transverse direction (Y). In such embodiments, within a single elastomeric panel, 140 and/or 150, a portion of the second portion, 146 and/or 156, of the elastomeric panel, 140 and/or 150, respectively, where there is no overlap with the absorbent core 56 may have a uniform tension in the transverse direction (Y) and a portion of the second portion, 146 and/or 156, of the elastomeric panels, 140 and/or 150, respectively wherein there is an overlapping configuration with the absorbent core 56 may have a non-uniform tension in the transverse direction (Y). As described herein, the absorbent core 56 need not have a second portion extending into an overlapping configuration with either the front region 20 or the back region 30 and therefore, the tension of the elastomeric panels, 140 and 150, can be uniform in each of the transverse direction (Y).

In various embodiments, it may be deemed suitable to vary the tension of the elastic material of the elastomeric panels, 140 and/or 150, in the longitudinal direction (X) even in the absence of an overlapping configuration with an absorbent core 56. While the elastic material in each of the elastomeric panels, 140 and 150, can continuously extend between each of the first side edges, 24 and 34, respectively, and the second side edges, 26 and 36, respectively, to maintain continuous tension of the elastic material in the transverse direction (Y) of the absorbent article 10, in various embodiments, it may be desirable to vary the tension of the elastic material in the longitudinal direction (X) of the absorbent article 10. Varying the tension of the elastic material in the longitudinal direction (X) of the absorbent article 10 can allow regions of the absorbent article 10 to react independently from other regions of the absorbent article 10 in response to strain placed on a particular region of the absorbent article 10 by the wearer of the absorbent article 10 providing for an improvement in the close-to-body-fit of the absorbent article 10. Wearers of absorbent articles 10 come in a variety of shapes and sizes and providing an absorbent article 10 with variable tension strains in the longitudinal direction (X) can allow the absorbent article 10 to better conform to the curvature of the body of the wearer. Varying the tension of the elastic material in the longitudinal direction (X) of the absorbent article 10 also allows for the wearer of the absorbent article 10 to comfortably experience a tension in the regions where the elastomeric panels, 140 and 150, overlap with the absorbent core 56 of the absorbent article 10. The absorbent core 56 has a thickness dimension in the depth direction (Z) of the absorbent article 10 and a wearer may experience discomfort while wearing the absorbent article 10 if the same tension maintaining the elastomeric panels, 140 and 150, in a close-to-body-fit in regions not overlapping the absorbent core 56 were used to maintain the overlapping region in a close-to-body-fit. Such discomfort may result from the absorbent core 56 being pulled too close to the body of the wearer. Varying the tension of the elastic material within each of the elastomeric panels, 140 and 150, can occur by varying the number of elastic materials, decitex, spacing, or elongation stress during formation of the elastic materials.

Referring to FIGS. 1-4, the elastomeric panels, 140 and 150, of the front region 20 and the back region 30, respectively, can be constructed of a laminate that has multiple elastomeric strands 160 which can be sandwiched between two nonwoven web layers, 162 and 164. Each of the elastomeric panels, 140 and 150, can have a first portion, 144 and 154, respectively, which can be the waist portion of the absorbent article 10. The elastomeric strands 160 of the front waist portion 144 can be aligned parallel with each other and can be uniformly spaced apart from each other. In various embodiments, the spacing between each elastomeric strand 160 within the front waist portion 44 can be less than about 4 or 3 mm. The elastomeric strands 160 of the back waist portion 154 can be aligned parallel with each other and can be uniformly spaced apart from each other. In various embodiments, the spacing between each of the elastomeric strands 160 of the back waist portion 154 can be less than about 4 or 3 mm. In various embodiments, when the absorbent article 10 is in a usage configuration, the elastomeric strands 160 of the front waist portion 144 can be aligned with the elastomeric strands 160 of the back waist portion 154.

Referring to FIGS. 1, 3, and 4, the elastomeric panel 140 of the front region 20 can have a second portion 146 which can be the chassis portion of the front region 20. The elastomeric strands 160 of the second portion 146 can be aligned parallel with each other can be uniformly spaced apart from each other. In various embodiments, the spacing between each elastomeric strand 160 within the second portion 146 of elastomeric panel 140 of the front region 20 can be greater than about 5, 6, 7, 8, or 9 mm. As the spacing of the elastomeric strands 160 in the front waist portion 144 of the front region 20 are smaller than the spacing of the elastomeric strands 160 of the second portion 146 of the elastomeric panel 140 of the front region 20, the front waist portion 144 can have a tension which can be higher than the tension of the second portion 146 of the elastomeric panel 140 of the front region 20. The higher tension of the front waist portion 144 can help to maintain the absorbent article 10 in place about the waist of the wearer of the absorbent article 10. The second portion 146 of the elastomeric panel 140 of the front region 20 can have a portion 148 within which is located a portion of the absorbent core resulting in an overlapping configuration with the absorbent core 56. The portion 148 which contains an overlapping configuration with the second portion of the absorbent core 56 can have a non-uniform tension in the transverse direction (Y) from the first side edge 24 to the second side edge 26 while the remainder of the second portion 146 of the elastomeric panel 140 can have a uniform tension in the transverse direction (Y) as it does not contain an overlapping configuration with the second portion of the absorbent core 56.

Referring to FIGS. 2-4, the elastomeric panel 150 of the back region 30 can have a second portion 156 which can be the chassis portion of the back region 30. The elastomeric strands 160 of the second portion 156 of the elastomeric panel 150 of the back region 30 can be aligned parallel with each other, however, they need not be uniformly spaced from each other. The non-uniformity in spacing of the elastomeric strands 160 can provide the elastomeric panel 150 of the back region 30 with non-uniform tensioning in the longitudinal direction (X) of the elastomeric panel 150 of the back region 30. For example, in the exemplary embodiment illustrated in FIGS. 2-4, the second portion 156 of the elastomeric panel 150 of the back region can have three segments wherein within each segment, the elastomeric strands 160 are aligned parallel with each other and the spacing of the elastomeric strands 160 within the segment is uniform. However, the spacing of the elastomeric strands 160 within one segment is different than the spacing of the elastomeric strands 160 within a different segment of the second portion 156 of the elastomeric panel 150 of the back region 30. While FIGS. 2-4 provide an illustration of an elastomeric panel 150 of the back region 30 having three segments of non-uniform tensioning in the longitudinal direction (X) in the second portion 156 of the elastomeric panel 150, it is to be understood that the second portion 156 of the elastomeric panel 150 of the back region 30 can have at least 2, 3, 4, or 5 segments of non-uniform tensioning in the longitudinal direction (X). As illustrated in the exemplary embodiment illustrated in FIGS. 2-4, a first segment 170 positioned adjacent to the back waist portion 154 has multiple elastomeric strands 160 which are uniformly spaced apart from each other. The uniform spacing of the elastomeric strands 160 in the first segment 170 can be 5, 6, or 7 mm. A second segment 172 located closest to and/or in an overlapping configuration with the absorbent core 56 can have multiple elastomeric strands 160 which are uniformly spaced apart from each other and the uniform spacing of the elastomeric strands can be greater than 15 mm. A third segment 174 is positioned between the first segment 170 and the second segment 172 and has multiple elastomeric strands 160 which are uniformly spaced apart from each other and the uniform spaced can be 7, 8, 9, or 10 mm. As illustrated in the exemplary embodiment, the first segment 170 can have more elastomeric strands 160 which are spaced closer together than either the second segment 172 or the third segment 174. The second segment 172 can have the least number of elastomeric strands which are spaced the farthest apart from each other than either the first segment 170 or the third segment 174. In the exemplary embodiment illustrated in FIGS. 2-4, spacing of the elastomeric strands can provide the non-uniform tensioning in the longitudinal direction (X) of the second portion 156 of the elastomeric panel 150 of the back region 30. Additionally, the elastomeric panel 150 of the back region 30 can have a portion 176 within which is positioned a third portion of the absorbent core 56 resulting in an overlapping configuration with the third portion of the absorbent core 56. The portion 176 which contains an overlapping configuration with the third portion of the absorbent core 56 can have a non-uniform tension in the transverse direction (Y) from the first side edge 34 to the second side edge 36 while the remainder of the second portion 156 of the elastomeric panel 150 can have a uniform tension in the transverse direction (Y) as it does not contain an overlapping configuration with the third portion of the absorbent core 56.

Figure 7:
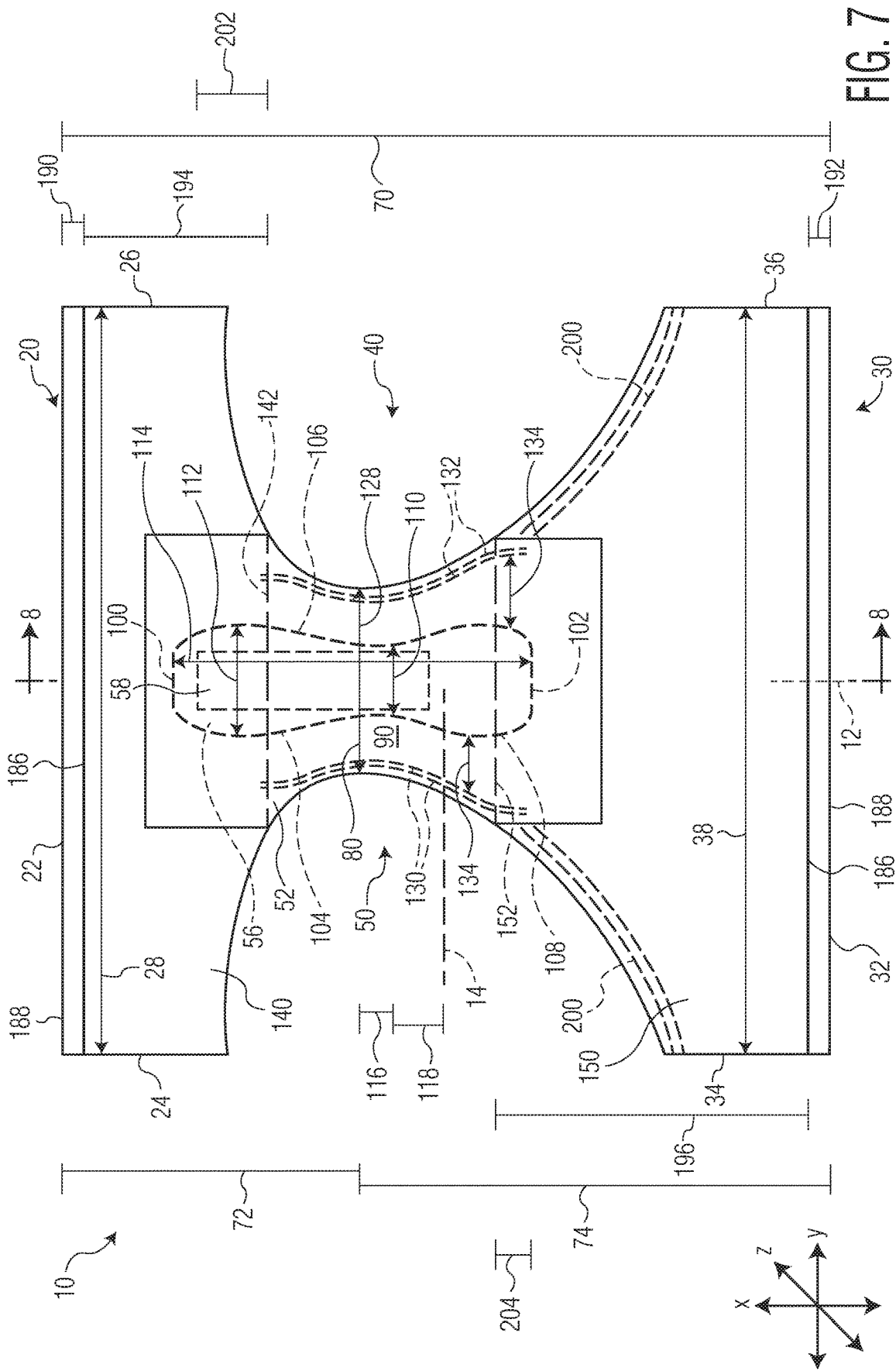
FIG. 7 is an illustration of a plan view of an alternate embodiment of an absorbent article in a longitudinally and transversely stretched and laid-flat configuration prior to the joining of the front and back regions with the surface of the absorbent article that faces the wearer when the absorbent article is worn facing the viewer.
Figure 8:
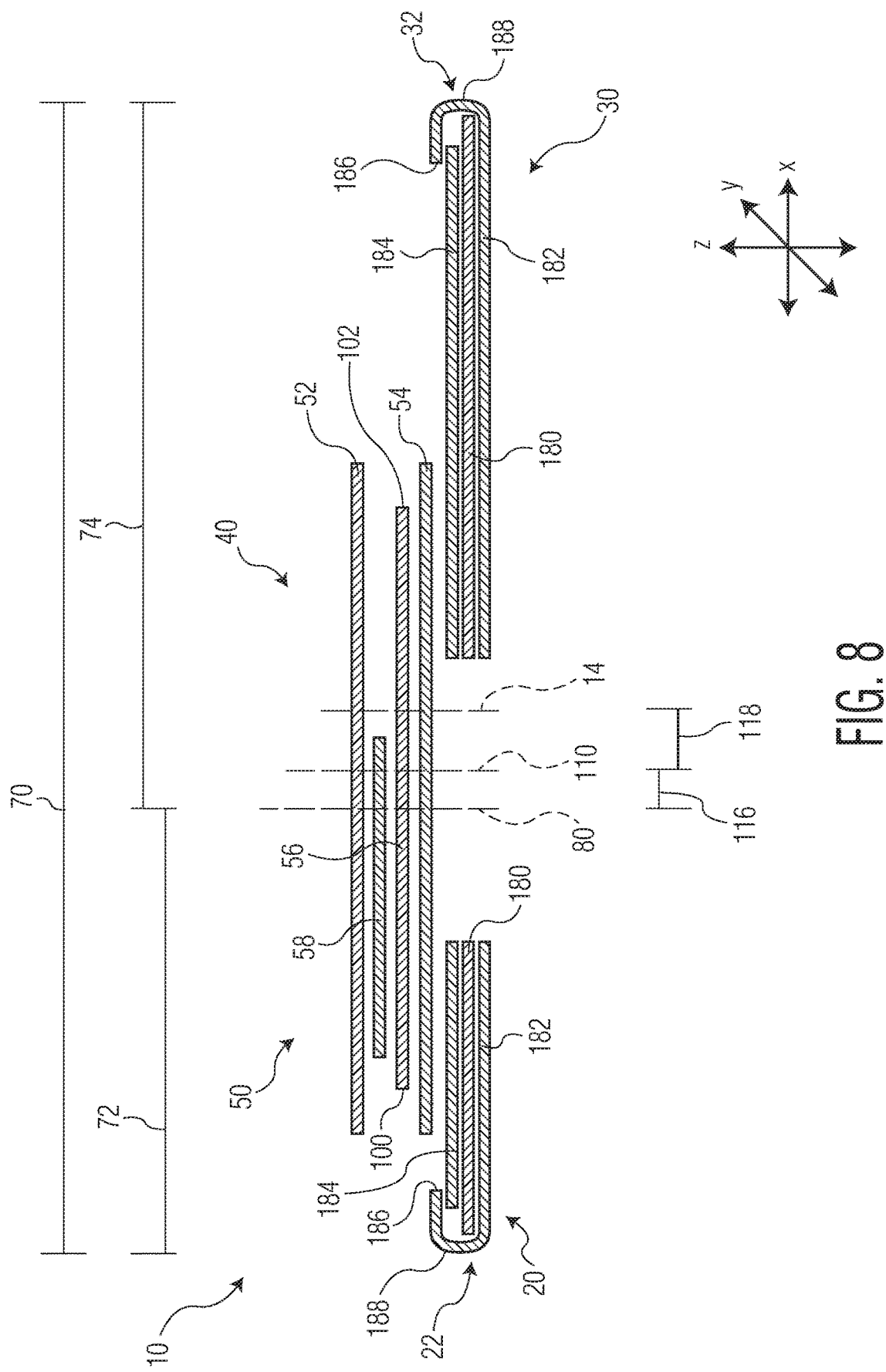
FIG. 8 is an illustration of a cross-sectional view of an embodiment of the absorbent article of FIG. 7 taken along line 8-8.

FIGS. 7 and 8 provide an alternate illustration of an exemplary embodiment of an absorbent article 10 wherein the elastic material within the elastomeric panels, 140 and 150, of the front region 20 and back region 30, respectively, is a polymeric film material 180 which can be sandwiched between two nonwoven layers, 182 and 184. Each of the elastomeric panels, 140 and 150, can have a first portion, 190 and 192, respectively, which can be the waist portion of the absorbent article 10. In various embodiments, when the absorbent article 10 is in a usage configuration, the waist portions, 190 and 192, can be aligned with each other. In various embodiments, each first portion, 190 and 192, of the elastomeric panels, 140 and 150, respectively, can have a length in the longitudinal direction (X) which is less than about 5, 4, or 3% of the absorbent article length 70. In the illustrative exemplary embodiments of FIGS. 7 and 8, the first portion, 190 and 192, can be further illustrated as the elastic material 160 sandwiched between the first nonwoven layer 182 which has been folded over onto itself creating a fold 188 and placing a material edge 186 on the interior of the absorbent article 10. In various embodiments, the elastic material in each of the first portions, 190 and 192 of the elastomeric panels, 140 and 150, can have a uniform tension in the transverse direction (Y) and in the longitudinal direction (X).

The elastomeric panel 140 of the front region 20 can have a second portion 194 which can be the chassis portion of the front region 20. The second portion 194 of the elastomeric panel 140 of the front region 20 can have a portion 202 within which is contained a second portion of the absorbent core 56 resulting in an overlapping configuration with a second portion of the absorbent core 56. The portion 202 which contains an overlapping configuration with the second portion of the absorbent core 56 can have a non-uniform tension in the transverse direction (Y) from the first side edge 24 to the second side edge 26 while the remainder of the second portion 194 of the elastomeric panel 140 can have a uniform tension in the transverse direction (Y) as it does not contain an overlapping configuration with the second portion of the absorbent core 56. The elastomeric panel 150 of the back region 30 can have a second portion 196 which can be the chassis portion of the back region 30. The second portion 196 of the elastomeric panel 150 of the back region 30 can have a portion 204 within which is contained a third portion of the absorbent core 56 resulting in an overlapping configuration with a third portion of the absorbent core 56. The portion 204 which is contained an overlapping configuration with the third portion of the absorbent core 56 can have a non-uniform tension in the transverse direction (Y) from the first side edge 34 to the second side edge 6 while the remainder of the second portion 196 of the elastomeric panel 150 can have a uniform tension in the transverse direction (Y) as it does not contain an overlapping configuration with the third portion of the absorbent core 56.

As described herein, in various embodiments, it may be desirable to vary the tension of the elastomeric panel, 140 and/or 150, in the longitudinal direction (X). In various embodiments, the tension of a polymeric film material can be varied via utilizing multiple polymeric film materials arranged in a side-by-side manner in the longitudinal direction (X) wherein each polymeric film material has a different elastic characteristic from the adjacent polymeric film material. In various embodiments, the tension can be varied via the formation process of the elastomeric panel 150 in which a single polymeric film material is subjected to variable stretch during manufacturing thereby varying the tension in the polymeric film material.

Figure 9:
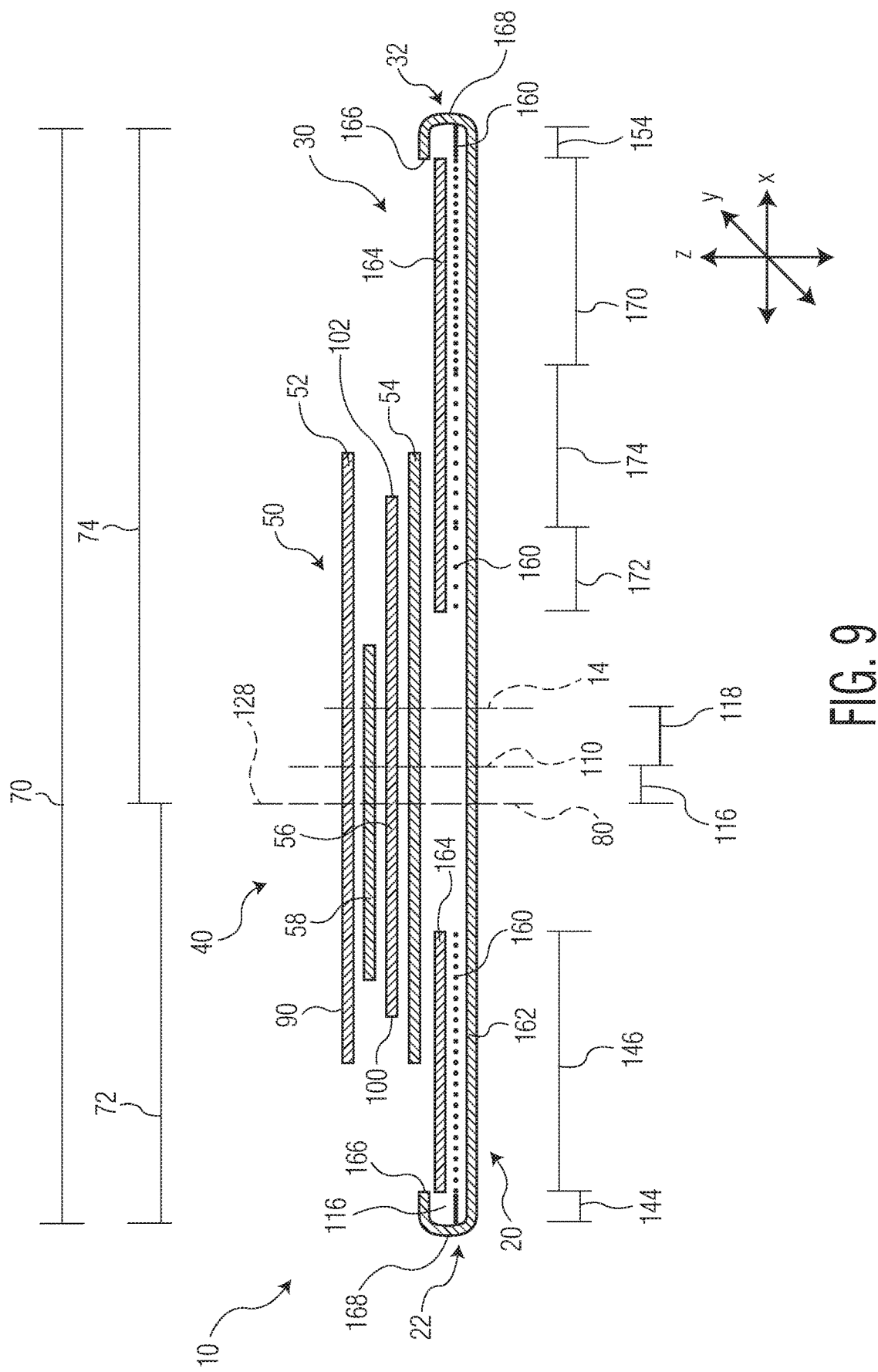
FIG. 9 is an illustration of a cross-sectional view of an alternate embodiment of the absorbent article of FIG. 3 taken along line 9-9.
Figure 10:
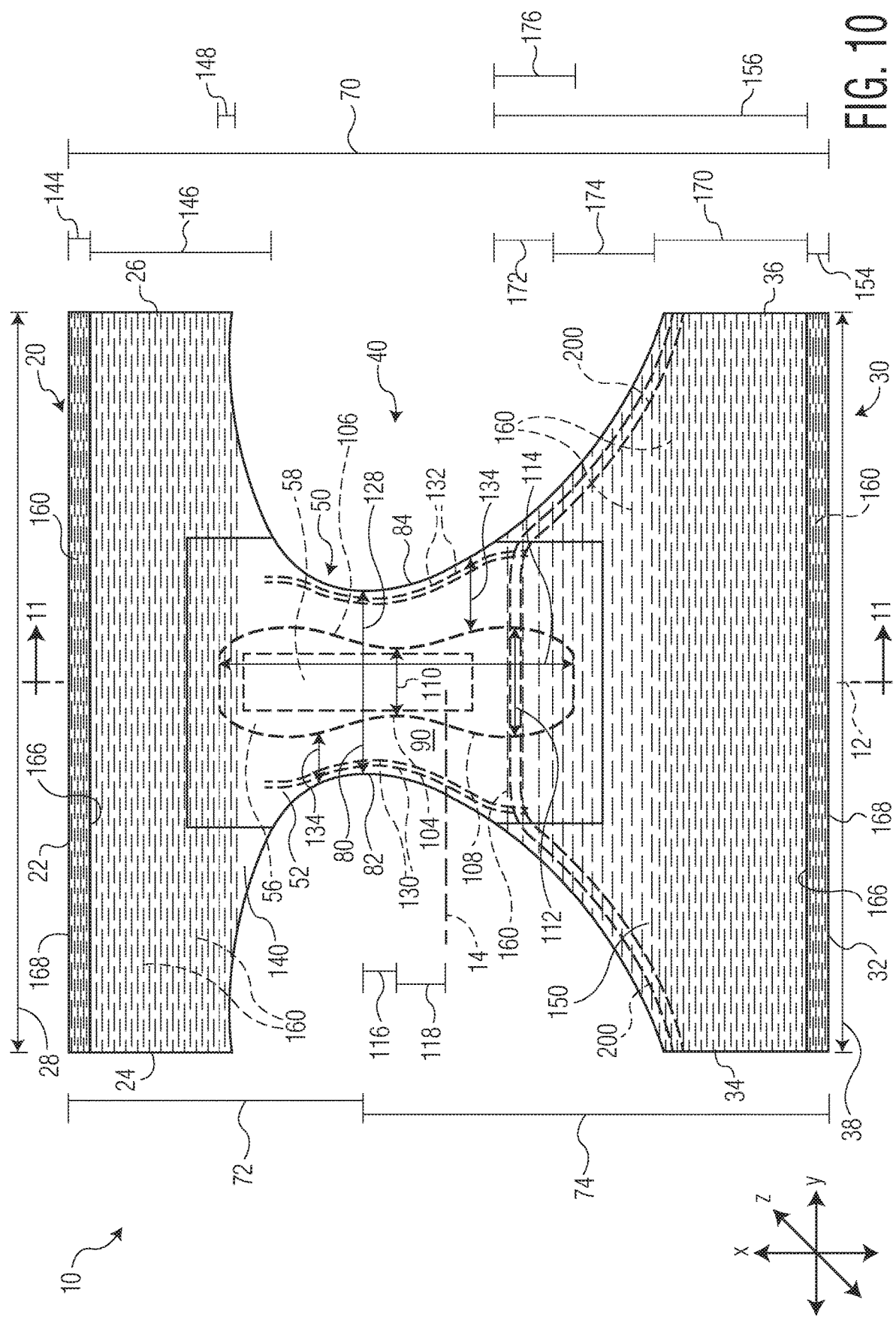
FIG. 10 is an illustration of a plan view of an alternate embodiment of an absorbent article in a longitudinally and transversely stretched and laid-flat configuration prior to the joining of the front and back regions with the surface of the absorbent article that faces the wearer when the absorbent article is worn facing the viewer.
Figure 11:
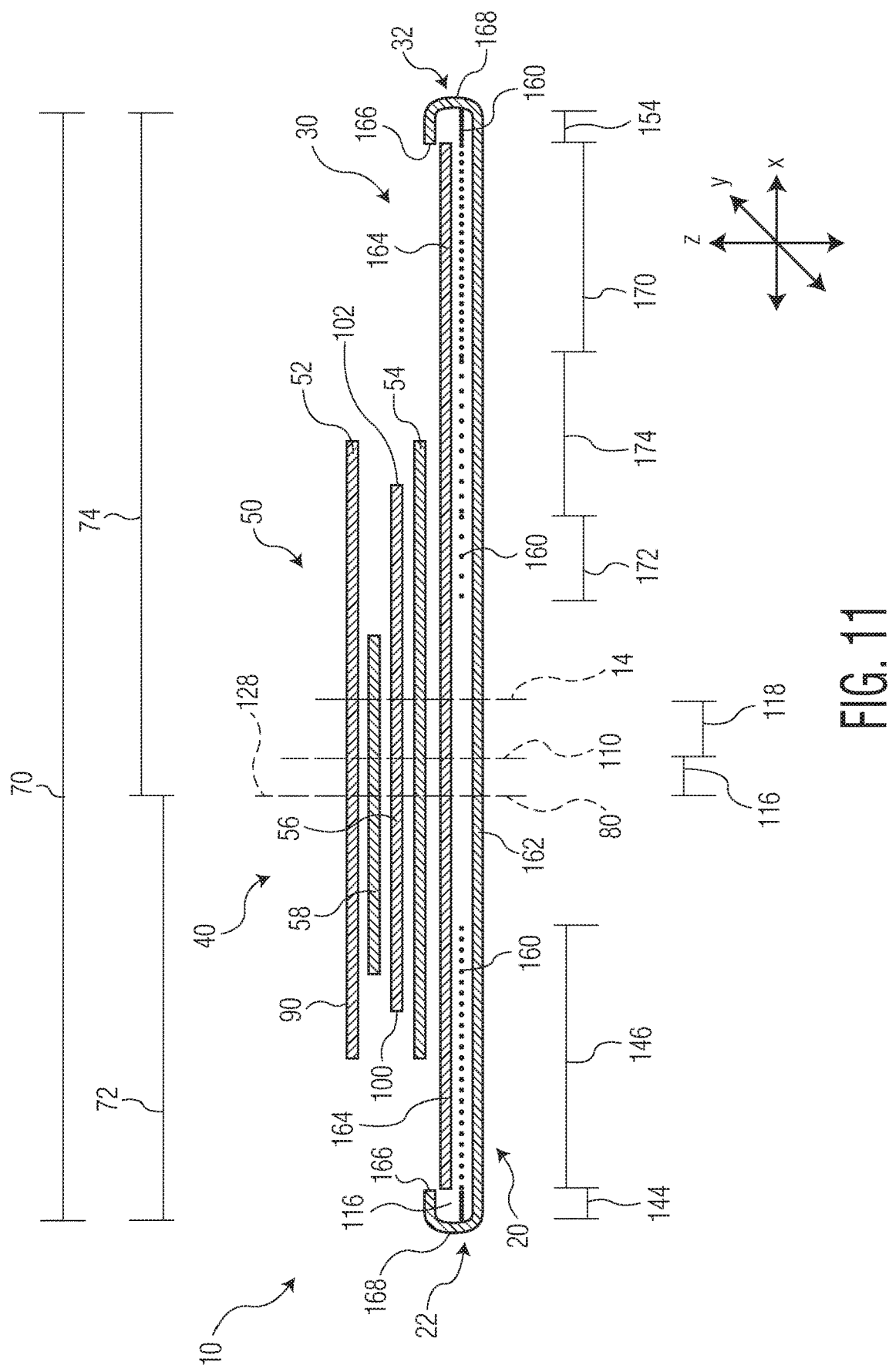
FIG. 11 is an illustration of a cross-sectional view of an embodiment of the absorbent article of FIG. 9 taken along line 10-10.

Referring to FIGS. 9-11, in various embodiments, the front region 20 and the back region 30 can be connected to each other via at least one of the materials forming the elastomeric panels, 140 and 150, respectively, of the front region 20 and the back region 30, respectively. FIG. 9 provides an exemplary illustration in which one of the nonwoven layers, such as nonwoven layer 162 is common to both elastomeric panels, 140 and 150, of each of the front region 20 and back region 30, respectively. FIGS. 10 and 11 provide an exemplary illustration of an absorbent article 10 in which both of the nonwoven layers, 162 and 164, are common to each of the elastomeric panels, 140 and 150, of the front region 20 and back region 30.

In various embodiments, the back region 40 can further have a leg elastic 200. In various embodiments, the back region 40 can have 1, 2, 3, 4, or 5 leg elastics 200. Each leg elastic 200 can be a single strand, ribbon, or strip of elastomeric material. For example, the back region 40 illustrated in FIG. 3 illustrates two strands of leg elastics 200. As the elastic material 160 of the elastomeric panel 150 of the back region 30 extends continuously from the first side edge 34 to the second side edge 36 thereby providing continuous tension to the elastomeric panel 150 of the back region 40, in various embodiments, it may be deemed suitable to alter the tension provided by the leg elastic 200 in order to reduce the amount of tension provided by the leg elastic 200. A reduction in the tension provided by the leg elastic 200 may be deemed suitable as the combination of the continuous tension provided by the elastic material 160 and the leg elastic 200 may result in bunching of the absorbent article 10 and protrusion of the absorbent article away from the body of the wearer of the absorbent article 10. In various embodiments, the tension provided by leg elastic(s) 200 may be altered by selectively deadening the leg elastic 200 such that the leg elastic 200 is no longer capable of exhibiting the ability to stretch and retract along its entire length. In various embodiments, selective deadening can occur via cutting the leg elastic 200 or mechanically altering the leg elastic 200. In various embodiments in which more than one leg elastic 200 is provided, each leg elastic 200 may have a tension different from the other leg elastic 200 such as, for example, a different decitex or a different elongation stress during formation. It is to be understood that the leg elastics 200 are optional.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any documents is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. An absorbent article comprising:
   a. a longitudinal direction and a transverse direction;
   b. a longitudinal axis and a transverse axis;
   c. a front region comprising a first waist edge, a first longitudinal direction side edge, a second longitudinal direction side edge transversely opposed to the first longitudinal direction side edge, a front region width in the transverse direction from the first longitudinal direction side edge to the second longitudinal direction side edge; a first waist portion, a first chassis portion, a first elastic material extending continuously in the transverse direction between the first longitudinal direction side edge and the second longitudinal direction side edge in the first chassis portion;
   d. a back region comprising a second waist edge, a third longitudinal direction side edge, a fourth longitudinal direction side edge transversely opposed to the third longitudinal direction side edge, a second waist portion, a second chassis portion, a second elastic material extending continuously in the transverse direction between the third longitudinal direction side edge and the fourth longitudinal direction side edge in the second chassis portion;
   e. a first side seam formed by bonding the first longitudinal direction side edge of the front region to the third longitudinal direction side edge of the back region and a second side seam formed by bonding the second longitudinal direction side edge of the front region to the fourth longitudinal direction side edge of the back region;
   f. a crotch region located between the front region and the back region and comprising an absorbent article narrowest width in the transverse direction wherein the absorbent article narrowest width is located between the transverse axis and the first waist edge;
   g. an article length measured from the first waist edge to the second waist edge;
   h. a first article sub-length measured from the first waist edge to the absorbent article narrowest width and a second article sub-length measured from the second waist edge to the absorbent article narrowest width wherein the first article sub-length is less than the second article sub-length;
   i. an absorbent core comprising:
      i. a perimeter edge comprising a first transverse direction end edge, a second transverse direction end edge opposed to the first transverse direction end edge; a first absorbent core longitudinal direction side edge, a second absorbent core longitudinal direction side edge opposed to the first longitudinal direction side edge, wherein the first longitudinal direction side edge and the second longitudinal direction side edge extend between and connect the first transverse direction end edge and the second transverse direction end edge, wherein the perimeter edge defines a non-rectangular shape of the absorbent core;
      ii. an absorbent core length measured from the first transverse direction end edge to the second transverse direction end edge wherein the absorbent core length is less than 50% of the article length;
      iii. a first portion of the absorbent core located in the crotch region;
      iv. a second portion of the absorbent core located in a portion of at least one of the front region or the back region wherein the second portion of the absorbent core is in an overlapping configuration with at least one of a portion of the first elastic material or a portion of the second elastic material;
      v. an absorbent core narrowest width measured in the transverse direction between the first absorbent core longitudinal direction side edge and the second absorbent core longitudinal direction side edge wherein the absorbent core narrowest width is located between the absorbent article narrowest width and the transverse axis; and
      vi. an absorbent core maximum width measured in the transverse direction between the first absorbent core longitudinal direction side edge and the second absorbent core longitudinal direction side edge;
   j. a first longitudinally extending elastic material located in the crotch region of the absorbent article and separated from the first longitudinal direction side edge of the absorbent core in the transverse direction at the location of each of the absorbent article narrowest width, the absorbent core narrowest width, and the transverse axis by a spatial distance of at least 1.5% of the front region width; and
   k. a second longitudinally extending elastic material location in the crotch region of the absorbent article and separated from the second longitudinal direction side edge of the absorbent core in the transverse direction at the location of each of the absorbent article narrowest width, the absorbent core narrowest width, and the transverse axis by a spatial distance of at least 1.5% of the front region width,
   wherein the first elastic material extends continuously in the transverse direction between the first longitudinal direction side edge and the second longitudinal direction side edge in the first chassis portion and over the absorbent core,
   wherein the second elastic material extends continuously in the transverse direction between the third longitudinal direction side edge and the fourth longitudinal direction side edge in the first chassis portion and over the absorbent core,
   wherein the second elastic material comprises a first segment comprising uniformly spaced elastomeric strands extending parallel to the transverse axis and a second segment comprising uniformly spaced elastomeric strands extending parallel to the transverse axis, the elastomeric strands of the second segment extending over the absorbent core and having a spacing between the elastomeric strands that is greater than a spacing between the elastomeric strands of the first segment.

2. The absorbent article of claim 1 wherein the absorbent article narrowest width is less than 25% of the front region width.

3. The absorbent article of claim 1 wherein the first article sub-length is less than 45% of the article length and the second article sub-length is greater than 55% of the article length.

4. The absorbent article of claim 1 wherein the absorbent core narrowest width is less than 12% of the front region width.

5. The absorbent article of claim 1 wherein the absorbent core narrowest width is less than 50% of the absorbent article narrowest width.

6. The absorbent article of claim 1 wherein the absorbent core maximum width is less than 25% of the front region width.

7. The absorbent article of claim 1 wherein the absorbent core narrowest width is less than 85% of the absorbent core maximum width.

8. The absorbent article of claim 1 wherein the absorbent core narrowest width is offset in the longitudinal direction from the absorbent article narrowest width by a distance from 1% to 5% of the article length.

9. The absorbent article of claim 1 wherein the absorbent core narrowest width is offset in the longitudinal direction from the transverse axis by a distance from 6% to 15% of the article length.

10. The absorbent article of claim 1 wherein the first longitudinally extending elastic material and the second longitudinally extending elastic material are non-linear in the longitudinal direction.

11. The absorbent article of claim 1 wherein the first longitudinally extending elastic material and the second longitudinally extending elastic material are linear in the longitudinal direction.

12. The absorbent article of claim 1 wherein the first elastic material and the second elastic material comprise a plurality of elastomeric strands.

13. The absorbent article of claim 1 wherein the first elastic material and the second elastic material comprise a polymeric film sheet.

14. The absorbent article of claim 1 wherein a portion of at least one of the first chassis portion or the second chassis portion has a non-uniform tension in the transverse direction.

15. The absorbent article of claim 1 wherein a portion of at least one of the first chassis portion or the second chassis portion has a uniform tension in the transverse direction.

16. The absorbent article of claim 1 wherein a portion of at least one of the first chassis portion or the second chassis portion has a non-uniform tension in the longitudinal direction.

17. The absorbent article of claim 1 wherein a portion of at least one of the first chassis portion or the second chassis portion has a uniform tension in the longitudinal direction.

18. The absorbent article of claim 1 wherein the back region further comprises a first leg elastic having a first tension.

19. The absorbent article of claim 18 wherein the back region further comprises a second leg elastic having a second tension which is different from the first tension of the first leg elastic.

20. The absorbent article of claim 18 wherein the first leg elastic has been selectively deadened.

* * * * *